US006838239B1

(12) United States Patent
Zyskind

(10) Patent No.: US 6,838,239 B1
(45) Date of Patent: Jan. 4, 2005

(54) CHITOBIASE AS A REPORTER ENZYME

(75) Inventor: Judith W. Zyskind, La Jolla, CA (US)

(73) Assignee: San Diego State University Foundation, San Diego, CA (US)

(*) Notice: Subject to any disclaimer, the term of this patent is extended or adjusted under 35 U.S.C. 154(b) by 0 days.

(21) Appl. No.: 09/630,931

(22) Filed: Aug. 2, 2000

Related U.S. Application Data

(60) Provisional application No. 60/159,221, filed on Oct. 13, 1999.

(51) Int. Cl.[7] .......................... C12Q 1/18; C12N 9/00; C12N 9/36; C07H 21/04
(52) U.S. Cl. .......................... 435/6; 435/4; 435/183; 435/195; 435/200; 435/206; 435/207; 435/209; 435/69.1; 435/252.3; 435/320.1; 536/23.2; 536/23.4; 536/23.7; 536/24.1
(58) Field of Search ............................. 435/69.1, 183, 435/200, 252.3, 320.1, 4, 6, 195, 206, 207, 209; 536/23.2, 23.4, 23.7, 24.1

(56) References Cited

U.S. PATENT DOCUMENTS

| | | | |
|---|---|---|---|
| 4,259,442 A | 3/1981 | Gayral | |
| 5,401,629 A | 3/1995 | Harpold et al. | |
| 5,436,128 A | 7/1995 | Harpold et al. | |
| 5,587,292 A | 12/1996 | Laine et al. | |
| 5,602,020 A | 2/1997 | Laine et al. | |
| 5,693,519 A | 12/1997 | Laine et al. | |
| 2002/0058260 A1 | 5/2002 | Zyskind et al. | |

FOREIGN PATENT DOCUMENTS

| | | |
|---|---|---|
| WO | WO 98/02742 | 1/1998 |
| WO | WO 98/49320 | 11/1998 |
| WO | WO 99/14311 | 3/1999 |

OTHER PUBLICATIONS

Cid, et al., *Yeast*, 10:747–756, 1994, "Yeast Exo–β–glucanases can be used as efficient and readily detectable reporter genes in *Saccharomyces cerevisias*."*
Fang, et al., *Veterinary Microbiology*, 46:361–367, 1995, "A fluorometric β–glucuronidase assay for analysis of bacterial growth in milk."*
Hayashi, et al., *Biosci. Biotech. Biochem.*, 59(10):1981–1982, "Identification of the positions of disulfide bonds of chitinase from a marine bacterium, *Alteromonas sp.* strain O–7,"*
Mazmanian, et al., *PNAS*, 97(10):5510–5515, 2000, "*Staphylococcus aureus* sortase mutants defective in the display of surface proteins and in the pathogenesis of animal infections."*
Stathopoulos, C., *Membr. Cell Biol.*, 12(1):1–8, 1998, "Structural features, physiological roles, and biotechnological applications of the membrane proteases of the OmpT bacterial endopeptidase family: A micro–review."*
Brosius, J., et al., *J. Mol. Biol.*, 148:107–127, 1981, "Gene Organization and Primary Structure of a Ribosomal RNA Operon from *Escherichia coli*."
Chang and Cohen, *J. Bacteriol.*, 134(3):1141–1156, 1978.
"Construction and Characterization of Amplifiable Multilcopy DNA Cloning Vehicles Derived from the P15A Cryptic Miniplasmid."
Chiaramello & Zyskind, *J. Bacteriol.*, 172(4):2013–2019, 1992.
"Coupling of DNA Replication of Growth Rate in *Escherichia coli*: A Possible Role for Guanosine Tetraphosphate."
Dickson, R. C., et al., *Science*, 187:27–35, 1975.
"Genetic Regulation: The Lac Control Region."
Diederich, L., et al., *Plasmid*, 28:14–24, 1992.
"New Cloning Vectors for Integration into the λ Attachment Site attB of the *Escherichia coli* Chromosome."
Froelich, J. M., et al., *J. Bacteriol.*, 178(20):6006–6012, 1996.
"Fis Binding in the dnaA Operon Promoter Region."
Goodman, S. D., et al., *Proc. Natl. Acad. Sci. USA*, 89:11910–11914, 1992, "Deformation of DNA during Site–Specific Recombination of Bacteriophage Lambda: Replacement of IHF Protein by HU Protein or Sequence––Directed Bends."
Hansen, F. G., et al., *EMBO J.*, 1(9):1043–1048, 1982.
"The Nucleotide Sequence of the dnaA Gene Promoter and of the Adjacent rpmH Gene, Coding for the Ribosomal Protein L34, of *Escherichia coli*."
Jannatipour, M. et al., *J. Bacteriol.*, 169(8):3785–3791, 1987.
"Translocation of *Vibrio harveyi* N,N'–diacetylchitobiase to the Outer Membrane of *Escherichia coli*."
Kalabat, D. Y., et al., *BioTechniques*, 25(6):1030–1035, 1998.
"Chitobiase, A New Reporter Enzyme."
Messer, W. and C. Weigel, "Initiation of Chromosome Replication," in F. C. Neidhart, et al. (Eds.), *Escherichia coli and Salmonella and Molecular Biology*, pp. 1579–1601, ASM Press, Washington, D.C., 1996.
Miller, J. H., *A Short Course in Bacterial Genetics*, p. 73, CSH Laboratory Press, Cold Spring Harbor, NY, 1992.
Nagaraja, R. and R. A. Weisberg, *J. Bacteriol.*, 172(11):6540–6550, 1990.

(List continued on next page.)

*Primary Examiner*—Manjunath N. Rao
(74) *Attorney, Agent, or Firm*—Knobbe, Martens, Olson & Bear, LLP

(57) ABSTRACT

The present invention relates to reporter gene constructs encoding a cytoplasmic form of chitobiase (N,N'-diacetylchitobiase) and methods of using these reporter gene constructs. The use of a cytoplasmic form of chitobiase as a reporter enzyme is generally applicable to the study of gene expression in organisms which do not contain N-acetyl-β-D-glucosaminidases.

14 Claims, 5 Drawing Sheets

OTHER PUBLICATIONS

"Specificity Determinants in the Attachment Sites of Bacteriophages HK022 and λ."
Orosz, A., et al., *Eur. J. Biochem.*, 201:653–659, 1991.
"Analysis of the Complex Transcription Termination Region on the *Escherichia coli* rmB Gene."
Soto–Gil and Zyskind, "Cloning of *Vibrio harveyi* Chitinase and Chitobiase Genes in *Escherichia coli*." in J. P. Zikakis (Ed.), *Chitin, Chitosan, and Related Enzymes*, pp. 209–223, Academic Press, Inc., New York, 1984.
Soto–Gil and Zyskind, *J. Biol. Chem.*, 264(25):14778–14783, 1989.
"N,N'–Diacetylchitobiase of *Vibrio harveyi* Primary Structure, Processing, and Evolutionary Relationships."
Yanisch–Perron, C., et al., *Gene*, 33:103–119, 1985.
"Improved M13 Phage Cloning Vectors and Host Strains: Nucelotide Sequences of the M13mp18 and pUC19 Vectors."
Altschul, et al., *J. Mol. Biol*, 215:403–410, 1990, "Basic Local Alignment Search Tool.".
Ball, et al., *Journal of Bacteriology*, 174(24):8043–8056, 1992, "Dramatic Changes in Fis Levels upon Nutrient Upshift in *Escherichia coli*.".
Bernstein, H. D., *Current in Microbiology*, 3:203–209, 2000, "The Biogenesis and Assembly of Bacterial Mombrane Proteins.".
Biswas, et al., *Biochemistry*, 38:10919–10928, 1999, "Mechanism of DnaB Helicase of *Escherichia coli*: Structural Domains Involved in ATP Hydrolysis, DNA Binding, and Oligomerization.".
Bootsma, et al., *J. Bacteriol.*, 181(16):5090–5093, 1999, "*Moraxella (Branhamella) catarrhalis* BRO β–Lactamase: A Lipoprotein of Gram–Positive Origin?".
Braun, et al., *Cell*, 40–159–169, 1985, "Autoregulation of the DNA Replication Gene dnaA In *E. coli* K–12.".
Bunn, et al., *FEMS Microbiol. Lett*, 165:123–127, 1998, "Wall–associated Processing of Extracellular Enzmes of *Staphylococcus Simulans Blovar Staphylolyticus*.".
Cámara, et al., *Infection and Immunity*, 62(9):3888–3895, 1994, "A Neutaminidase from *Streptococcus pneummoniae* Has the Features of a Surface Protein.".
Chamberlain, et al., *J. Med. Microbiol.*, 44(2):125–129, 1996, "Genetic Regulation of Fatty Acid Modifying Enzyme from Staphylococcus aureus.".
Chmourguina, et al., *Infection and Immunity*, 64(7):2387–2390, 1998, "Conservation of the C5a Pepdase Genes in Group A and B Streptococci.".
Churchill, et al., *Nucleic Acids Research*, 18(3):589–597, 1989, "The Distribution of Reconstriction Enzyme Sites in *Escherichia coli*.".
Clarke, et al., *Journal of Biological Chemistry*, 270(15):8805–8814, 1995, "Cloning of the β–N–Acetylglucosaminktase Gene from *Streptoccus pneumoniae*.".
Cohen–Kuplec, et al., *Curr. Opin. Biotechnol.*, 9(3):270–277, 1998, "The Molecular Biology of Chltin Digestion.".
Daugherty, et al., *Protein Engineering*, 12(7):613–621, 1999, "Development of an Optimized Expression System for the Screening of Antibody Libraries Displayed of the *Escherichia coil* surface.".
Dekker, N., *Molecular Microbiology*, 35(4):711–717, 2000, "Outer–membrane Phospholipase A: Known Structure, Unknown Biological Function.".

den Hollander, et al., *Antimicrobial Agents and Chemotherapy*, 21(1):95–100, 1997, "Synergism between Tobramycin and Ceflzaidime against a Resistant *Psudomonas aeruglnosa* Strain, Tested in an in Vitro Pharmacokinetic Model.".
Diederich, et al., *Bio Techniques*, 16(5):916–923, 1994, "A Versatile Plasmid Vector System for the Regulated Expression of Genes in *Escherichia coli*.".
Doem, et al., *Antimicrobial Agents and Chemotherapy*, 32(12): 1747–1753, 1988, "Antimicrobial Susceptibility Testing of *Haemophilus influenzae, Branhamella catarrhalis*, and *Neisseria gonorrhoeae*.".
Fricke, et al., *Biocimica et Biophysica Acta*, 1454:238–250, 1999, "Characterization and Purification of an Outer Membrane Metaliproteinase from Pseudomonas aeruginosa with Fibrinogenotytic Activity.".
Giraudo, et al., *Can. J. Microbiol.*, 40:677–681, 1994, "Characterization of a Tn551–mutant of *Staphylococcus aureus* Defective in the Production of Several Exproteins.".
Götz, et al., *Chemistry and Physics of Lipids*, 93:15–25, 1998, "Staphylococcal Lipases: Molecular Characterisation, Secretion, and Processing.".
Groicher, et al., *Journal of Bacteriology*, 182(7):1801, 2000, "The *Staphylococcus aureus* IrgAB Operon Modulates Murein Hydrolase Activity and Penicillin Tolerance.".
Gutmann, et al., *Antimicrobial Agents and Chemotherapy*, 30(6):906–912, 1986, "Involvement of Penicillin–Binding Protein 2 with Other Penicillin–Binding Proteins in Lysis of *Echerichia coli* by Some β–Lactam Antibiotics Alone in Synergistic Lytic Effect of Amdinocillin (Mecillinam).".
Hansen, et al., *Nucleic Acids Research*, 10(22):7373–7385, 1982, "The Nucleotide Sequence of the dnaA Gene and the First Part of the dnaN Gene of *Escherichia coli* K–12.".
Hiasa, et al., *Journal of Biological Chemistry*, 274(38):27244–27248, 1999, "Initiation of Bidirectional Replication at the Chromosomal Origin is Directed by the Interaction between Helicase and Primase.".
Igarashi, et al., *Microbiol. Imunol.*, 36(6):643–647, 1992, "Characterization of and Exo–β–O–Fructosidase from *Streptococcus mutans* Ingbritt.".
Igarashi, et al., *Microbiol. Imunol.*, 36(9):969–976, 1992, "Characterization of the Dextranase Purified from *Streptococcus mutans* Ingbritt.".
Mazmanian, et al., *Science*, 285:760–783, 1999, "*Staphylococcus aureus* Sorlase, an Enzyme that Anchors Surface Proteins to the Cell Wall.".
Navara, et al., *Microbiology and Molecular Biology Reviews*, 83(1):174–229, 1999, "Surface Proteins of Gram––Positive Bacteria and Mechanisms of Their Targeting to the Cell Wall Envelope.".
Olsson–Liliquist, et al., *Scand. J. Infect. Dis. Suppl.*, 105:13–23, 1997, "Antimicrobial Susceptibility Testing in Sweden: III. Methodology for Susceptibility Testing.".
Oshida, et al., *Proc. Natl. Acad. Sci. USA*, 92:285–289, 1995, "A *Straphyfoccus aureus* Autolysin that has an N–acetylmuramoyl–Laianine Amidase Domain and an Endo–β–N–acetylglucosaminidase Domain: Cloning, Sequence Analysis, and Characterization.".
Piruzlan, et al., *Molecular & General Genetics*, 257(5):561–567, 1998, "The Use of a Thermostable Beta–glucanase Gene from Clostridium Thermocellum as a Reporter Gene in Plants." *Database Blosis Online! Biosciences Information Service*, Abstract, XP002171323.

Reilly, et al., *Journal of Bacteriology*, 181(21):6797–6805, 1999, "Outer Membrane Lipoprotein e (P4) of *Haemophilus influenze* is a Novel Phosphomonoesterase.".

Reilly, et al., *Protein Expression and Purification*, 17:401–409, 1999, "Purification and Characterization of a Recombinant *Haemophilus influenzae* Outer Membrane Phosphomonoesterase e (P4).".

San Martin, et al., *Structure*, 6(4):501–509, 1998, "Three–dimensional Reconstructions from Cryoelectron Microscopy Images Reveal an Intimate Complex Between Hellcase DnaB and its Loading Partner DnaC.".

Schalk, et al., *Biochemistry*, 38:9357–9365, 1999, "Copurification of the FpvA Ferric Pyoverdin Receptor of *Psuedomonas aeruginosa* with its Iron–Free Ligand: Implications for Siderophore–Mediated Iron Transport.".

Shipman, et al., *Journal of Bacteriology*, 181(23):7206–7211, 1999, "Physiological Characterization of SusG, an Outer Membrane Protein Essential for Starch Utilization by Bacteriodes thetalotaomicron.".

Siezen, R.J., *Antonie van Leeuwenhoek*, 76:139–155, 1999, "Multi–domain, Cell–envelope Proteinases of Lactic Acid Bacteria.".

Sivapresasarao, et al., *Biochem. J.*, 296:209–215, 1993, "Expression of Functional Human Retinol–binding Protein in *Escherichia coli* Using a Secretion Vector.".

Smith, et al., *Diagn. Microbiol. Infect. Dis.*, 27:85–92, 1997, "Assessment of the Synergistic Interactions of Levofloxacin and Ampicillin Against *Enterococcus taecium* by the Checkarboard Agar Dilution and Time–Kill Methods.".

Smith, et al., *Infection and Immunity*, 60(6):2361–2367, 1992, "Cloning and Nucleotide Sequence of the Gene Encoding the 138–Kilodallon Surface Protein (Muramidase–Released Protein) of *Streptococcus suis* Type 2.".

Solo–Gil, et al., in "Methods of Enzymology." vol. 161, 1998. "N N'–Diacetylchitobase of Vibro harveyi," pp. 524–529, Academic Press, Inc., New York.

Stathopoulos, C., *Membr. Cell Biol.*, 13(1):3–21, 1999, "Bacterial Outer Membrane Proteins: Topological Analyses and Biotechnological Perspectives.".

Stanberg, et al., *Journal of Biological Chemistry*, 269(18):13468–13464, 1994, "Molecular Characterization of Protein Sir, a Streptococcal Cell Surface Protein That Binds Both Immunoglobulin A and Immunoglobulin G.".

Striebel, et al., *Eur. J. Biochem.*, 262:832–839, 1999, "Eukaryotic Precursor Proteins are Processed by *Escherichia coll* Outer Membrane Protein OmpP.".

Suciu, et al., *Molecular Microbiology*, 21(1):181–195, 1996, "The 19–residue Pro–peptide of Staphylococcal Nuclease has a Profound Secretion–Enhancing Ability in *Escherichia coli*.".

Sutton, et al., *Journal of Biological Chemistry*, 273(51):34255–34262, 1998, "*Escherichia coli* DnaA Protein: The N–Terminal Domain and Loading of DnaB Helicase at the *E. coli* Chromosomal Origin.".

Talon, et al., *International Journal of Food Microbiology*, 36:207–214, 1997, "Hydrolysis of Esters by Staphylococci.".

van der Meer, et al., *Journal of Bacteriology*, 175(g):2578–2588, 1993, "Characterization of the *Lactococcus laclis* Nisin A Operon Genes nisP, Encoding a Sublilisin–Like Serine Protease Involved in Precursor Processing, and nisR, Encoding a Regulatory Protein Involved in Nisin Biosynthesis.".

Wanda, et al., *Journal of Bacteriology*, 176(13):3839–3850, 1994, "Purification and Characterization of *Streplococcus sobrinus* Dextranase Produced in Recombinant *Escherichia coli* and Sequence Analysis of the Dextranase Gene.".

Weschler, et al., *Molec. Gen. Genetics*, 13:273–284, 1971, "*Eschericichia coli* Mutants Temperature–Sensitive for DNA Synthesis.".

International Search Report from foreign counterpart Application No. PCT/US00/21048 dated Jul. 23, 2001.

* cited by examiner

SEQUENCE LISTING

<160> NUMBER OF SEQ ID NOS: 19

<210> SEQ ID NO 1
<211> LENGTH: 29
<212> TYPE: DNA
<213> ORGANISM: Artificial Sequence
<220> FEATURE:
<223> OTHER INFORMATION: Oligonucleotide

<400> SEQUENCE: 1
gcacatgcat gctggtcatt aaattttcc                              29

<210> SEQ ID NO 2
<211> LENGTH: 26
<212> TYPE: DNA
<213> ORGANISM: Artificial Sequence
<220> FEATURE:
<223> OTHER INFORMATION: Oligonucleotide

<400> SEQUENCE: 2
cggggtacca actcatcctg caatcg                                 26

<210> SEQ ID NO 3
<211> LENGTH: 28
<212> TYPE: DNA
<213> ORGANISM: Artificial Sequence
<220> FEATURE:
<223> OTHER INFORMATION: Oligonucleotide

<400> SEQUENCE: 3
ctagtctaga tgccgaactc agaagtga                               28

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide

<400> SEQUENCE: 4
gcacatgcat gcgggggatg gcttgtagat                             30

<210> SEQ ID NO 5
<211> LENGTH: 25
<212> TYPE: DNA
<213> ORGANISM: Artificial Sequence
<220> FEATURE:
<223> OTHER INFORMATION: Oligonucleotide

<400> SEQUENCE: 5
catgatcatg cgacaggttt gatga                                  25

<210> SEQ ID NO 6

-continued

```
<211> LENGTH: 22
<212> TYPE: DNA
<213> ORGANISM: Artificial Sequence
<220> FEATURE:
<223> OTHER INFORMATION: Oligonucleotide

<400> SEQUENCE: 6
gggggcgcct acctttcacg ag                                              22

<210> SEQ ID NO 7
<211> LENGTH: 26
<212> TYPE: DNA
<213> ORGANISM: Artificial Sequence
<220> FEATURE:
<223> OTHER INFORMATION: Oligonucleotide

<400> SEQUENCE: 7
catgcatgca tgaaacgatg gacacc                                          26

<210> SEQ ID NO 8
<211> LENGTH: 26
<212> TYPE: DNA
<213> ORGANISM: Artificial Sequence
<220> FEATURE:
<223> OTHER INFORMATION: Oligonucleotide

<400> SEQUENCE: 8
cggggtacca actcatcctg caatcg                                          26

<210> SEQ ID NO 9
<211> LENGTH: 12
<212> TYPE: DNA
<213> ORGANISM: Artificial Sequence
<220> FEATURE:
<223> OTHER INFORMATION: Oligonucleotide

<400> SEQUENCE: 9
cattaatgca tg                                                         12

<210> SEQ ID NO 10
<211> LENGTH: 12
<212> TYPE: DNA
<213> ORGANISM: Artificial Sequence
<220> FEATURE:
<223> OTHER INFORMATION: Oligonucleotide

<400> SEQUENCE: 10
cattaatgca tg                                                         12

<210> SEQ ID NO 11
<211> LENGTH: 5826
<212> TYPE: DNA
<213> ORGANISM: Artificial Sequence
<220> FEATURE:
<223> OTHER INFORMATION: pDYK9

<400> SEQUENCE: 11
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
```

-continued

| | |
|---|---|
| ggtatcaaca gggacaccag gatttattta ttctgcgaag tgatcttccg tcacaggtat | 420 |
| ttattcggcg caaagtgcgt cgggtgatgc tgccaactta ctgatttagt gtatgatggt | 480 |
| gtttttgagg tgctccagtg gcttctgttt ctatcagctg tccctcctgt tcagctactg | 540 |
| acggggtggt gcgtaacggc aaaagcaccg ccggacatca gcgctagcgg agtgtgcggc | 600 |
| cgcactggct tactatgttg gcactgatga gggtgtcagt gaagtgcttc atgtggcagg | 660 |
| agaaaaaagg ctgcaccggt gcgtcagcag aatatgtgat acaggatata ttccgcttcc | 720 |
| tcgctcactg actcgctacg ctcggtcgtt cgactgcggc gagcggaaat ggcttacgaa | 780 |
| cggggcggag atttcctgga agatgccagg aagatactta acgggaagt gagagggccg | 840 |
| cggcaaagcc gttttttccat aggctccgcc cccctgacaa gcatcacgaa atctgacgct | 900 |
| caaatcagtg gtggcgaaac ccgacaggac tataaagata ccaggcgttt ccctggcgg | 960 |
| ctccctcgtg cgctctcctg ttcctgcctt tcggtttacc ggtgtcattc cgctgttatg | 1020 |
| gccgcgtttg tctcattcca cgcctgacac tcagttccgg gtaggcagtt cgctccaagc | 1080 |
| tggactgtat gcacgaaccc cccgttcagt ccgaccgctg cgccttatcc ggtaactatc | 1140 |
| gtcttgagtc caacccggaa agacatgcaa aagcaccact ggcagcagcc actggtaatt | 1200 |
| gatttagagg agttagtctt gaagtcatgc gccggttaag gctaaactga aggacaagt | 1260 |
| tttggtgact gcgctcctcc aagccagtta cctcggttca aagagttggt agctcagaga | 1320 |
| accttcgaaa aaccgccctg caaggcggtt ttttcgtttt cagagcaaga gattacgcgc | 1380 |
| agaccaaaac gatctcaaga agatcatctt atgcggccgc atcagataaa atatttctag | 1440 |
| atgccgaact cagaagtgaa acgccgtagc gccgatggta gtgtggggtc tccccatgcg | 1500 |
| agagtaggga actgccaggc atcaaataaa acgaaaggct cagtcgaaag actgggcctt | 1560 |
| tcgttttatc tgttgtttgt cggtgaacgc tctcctgagt aggacaaatc cgccgggagc | 1620 |
| ggatttgaac gttgcgaagc aacggcccgg agggtggcgg gcaggacgcc cgccataaac | 1680 |
| tgccaggcat caaattaagc agaaggccat cctgacggat ggcctttttg cgtttctaca | 1740 |
| aactcttcct gtcgtcatat ctacaagcca tccccgcat gctggtcatt aaattttcca | 1800 |
| atatgcggcg taaatcgtgc ccgcctcgcg gcaggatcgt ttacacttag cgagttctgg | 1860 |
| aaagtcctgt ggataaatcg ggaaaatctg tgagaaacag aagatctctt gcgcagttta | 1920 |
| ggctatgatc cgcggtcccg atcgttttgc aggatcttga tcgggcatat aaccgcagac | 1980 |
| agcggttcgt gcgtcaccct caagcagggt cttttcgacg tacgtcaaca atcatgaatg | 2040 |
| tttcagcctt agtcattatc gacttttgtt cgagtggagt ccgccgtgtc actttcgctt | 2100 |
| tggcagcagt gtcttgcccg attgcaggat gagttggtac cgagctctga caacaagtt | 2160 |
| gtaaactcac tggctgataa ccttgatatc caatatgaag tgttaactaa ccatggtgct | 2220 |
| aacgaaggtc ttgcgtgcca agatatgggc gcagaatggg cttcttgtaa caaagtaaac | 2280 |
| atgacgcttg ttaaccaagg tgaagctgtt gactcaaaag attgggctat ttacttccac | 2340 |
| agcattcgtc tgattctgga tgttgacaac gagcagttca aaatctctcg tgtaacgggt | 2400 |
| gacctacata agctagaacc aacagataag tttgacggct tcgctgccgg tgaagaggtt | 2460 |
| gttcttccat tggttggtga atactggcaa ctatttgaaa ctgacttcat gccgggtgca | 2520 |
| ttcgtttctg ctccaaacgc agaacctaag atgattgctt ctctaaatac tgaagatgtt | 2580 |
| gcgtcttttg tgacgggtct tgaaggtaac aacctaaaac gtacaccaga tgacaacaat | 2640 |
| gtatttgcaa acgctgtgtc tcgttttgag aaaaacgaag acctagcaac acaagacgta | 2700 |

-continued

```
tcaaccacgt tactaccaac accaatgcac gttgaagcgg gtaaaggcaa agtagatatc    2760
gcggatggta ttgcgctgcc taaagacgca ttcgatgcga ctcagttcgc agcgattcaa    2820
gatcgtgcag aagtggtagg tgtggacgtt cgtggtgatc ttcctgtaag catcactgtt    2880
gttcctgcag acttcaccgg tgaattagca aaatctggtg cttacgaaat gagcatcaaa    2940
ggcgacggta ttgtgattaa agcgttcgac caagcaggcg ctttctacgc agtacaatct    3000
atctttggcc tggtagatag ccaaaatgct gattctctac cacaactgtc tattaaagat    3060
gcgcctcgtt ttgattaccg tggtgtgatg gtggatgtgg ctcgtaactt ccactctaag    3120
gacgcaatcc ttgcaacgct agaccaaatg gcagcgtaca agatgaacaa acttcacctt    3180
cacctaaccg atgatgaagg ctggcgttta gaaatcccgg gtctgcctga gctgacagaa    3240
gtgggtgcta accgttgttt cgatacacaa gagaaaagct gtttactgcc tcagcttggc    3300
tctggtccaa cgacagacaa ctttggctct ggctacttca gcaaagcaga ctacgtggaa    3360
atcttgaaat acgcgaaagc acgtaacatt gaagtgattc agaaatcga tatgccagct    3420
cacgctcgtg cagcagtagt atcaatggaa gctcgttacg accgcctaat ggaagaaggt    3480
aaagaagctg aagcgaacga ataccgtctg atggatcctc aagatacatc aaacgtaacg    3540
acggttcagt tctacaataa gcaaagcttc atcaacccat gtatggaatc ttcaactcgc    3600
tttgttgata aggtgatttc agaagtggca gcaatgcacc aagaagctgg cgctccacta    3660
acaacttggc acttcggtgg tgacgaagcg aagaacatca agctaggtgc tggtttccaa    3720
gacgttaacg cagaagataa agtaagctgg aaaggcacga ttgacctgtc taaacaagac    3780
aagccgtttg cacagtctcc acaatgtcag acgctaatca cagatggcac agtcagtgac    3840
tttgctcacc taccaagcca cttcgcggaa gaagtgtcga agattgttgc tgagaaaggc    3900
attccaaaact tccaagcttg gcaagatggt ttgaaataca gtgacggcga aaaagcgttc    3960
gctacagaaa atactcgcgt aaacttctgg gacgttctgt actggggcgg tacttcctca    4020
gtgtacgagt ggtctaagaa aggttacgac gtgattgttt ctaacccaga ttacgtgtac    4080
atggatatgc atacgaagt tgacccgaaa gagcgtggtt actactgggc aacacgtgca    4140
acggatactc gtaagatgtt tggctttgca ccagagaaca tgcctcaaaa cgcagaaact    4200
tctgtagatc gcgatggcaa tggctttact ggtaaaggtg aaatcgaagc gaaacctttc    4260
tacggtctat ctgcacaact ttggtctgag acagtacgta acgacgagca atacgagtac    4320
atggtattcc ctcgcgtcct cgctgctgct cagcgtgcat ggcaccgtgc tgactgggaa    4380
aacgactaca agttggtgt tgagtactcg caaaactcta atctagttga taaagcatcg    4440
ctaaaccaag actacaaccg ctttgcgaac gtacttggtc aacgtgaact ggctaagcta    4500
gaaaaatcag gtattgacta ccgcctacca gtaccaggtc aaaagtaga agatggtaag    4560
ctagcaatga acgttcagtt ccctggcgta acgcttcaat actctctgga tggtgagaac    4620
tggttgactt atgcagacaa cgctcgtcca aatgtaactg gtgaagtctt catccgctcg    4680
gtatctgcga caggtgagaa ggtaagccgt atcactagcg tgaaataata gcgctcagta    4740
ttcactaaaa tcatagttcc ttactcaaag ccctcaactt atgttggggg ctttgtttat    4800
ttttcttcgg aaaataagcg tgatcatgcg acaggtttga tgacaaaaaa ttagcgcaag    4860
aagacaaaaa tcaccttgcg ctaatgctct gttacaggtc actaatacca tctaagtagt    4920
tgattcatag tgactgcata tgttgtgttt tacagtatta tgtagtctgt tttttatgca    4980
aaatctaatt taatatattg atatttatat cattttacgt ttctcgttca gctttttat     5040
actaagttgg cattataaaa aagcattgct tatcaatttg ttgcaacgaa caggtcacta    5100
```

-continued

| | |
|---|---|
| tcagtcaaaa taaaatcatt atttgatttc aattttgtcc cactccctgc ctctgtcatc | 5160 |
| acgatactgt gatgccatgg tgtccgactt atgcccgaga agatgttgag caaacttatc | 5220 |
| gcttatctgc ttctcataga gtcttgcaga caaactgcgc aactcgtgaa aggtaggcgc | 5280 |
| ccccggtcga atttgctttc gaatttctgc cattcatccg cttattatca cttattcagg | 5340 |
| cgtagcacca ggcgtttaag ggcaccaata actgccttaa aaaaattacg ccccgccctg | 5400 |
| ccactcatcg cagtactgtt gtaattcatt aagcattctg ccgacatgga agccatcaca | 5460 |
| gacggcatga tgaacctgaa tcgccagcgg catcagcacc ttgtcgcctt gcgtataata | 5520 |
| tttgcccatg gtgaaaacgg ggcgaagaa gttgtccata ttggccacgt ttaaatcaaa | 5580 |
| actggtgaaa ctcacccagg gattggctga cgcaaaaac atattctcaa taaacccttt | 5640 |
| agggaaatag gccaggtttt caccgtaaca cgccacatct gcgaatata tgtgtagaaa | 5700 |
| ctgccggaaa tcgtcgtggt attcactcca gagcgatgaa aacgtttcag tttgctcatg | 5760 |
| gaaaacggtg taacaagggt gaacactatc ccatatcacc agctcaccgt ctttcattgc | 5820 |
| catacg | 5826 |

<210> SEQ ID NO 12
<211> LENGTH: 6071
<212> TYPE: DNA
<213> ORGANISM: Artificial Sequence
<220> FEATURE:
<223> OTHER INFORMATION: pDYK11

<400> SEQUENCE: 12

| | |
|---|---|
| gaattccgga tgagcattca tcaggcgggc aagaatgtga ataaaggccg gataaaactt | 60 |
| gtgcttattt ttctttacgg tctttaaaaa ggccgtaata tccagctgaa cggtctggtt | 120 |
| ataggtacat tgagcaactg actgaaatgc ctcaaaatgt tctttacgat gccattggga | 180 |
| tatatcaacg gtggtatatc cagtgatttt tttctccatt ttagcttcct tagctcctga | 240 |
| aaatctcgat aactcaaaaa atacgcccgg tagtgatctt atttcattat ggtgaaagtt | 300 |
| ggaacctctt acgtgccgat caacgtctca ttttcgccaa agttggccc agggcttccc | 360 |
| ggtatcaaca gggacaccag gatttattta ttctgcgaag tgatcttccg tcacaggtat | 420 |
| ttattcggcg caaagtgcgt cgggtgatgc tgccaactta ctgatttagt gtatgatggt | 480 |
| gtttttgagg tgctccagtg gcttctgttt ctatcagctg tccctcctgt tcagctactg | 540 |
| acggggtggt gcgtaacggc aaaagcaccg ccggacatca gcgctagcgg agtgtgcggc | 600 |
| cgcactggct tactatgttg gcactgatga gggtgtcagt gaagtgcttc atgtggcagg | 660 |
| agaaaaaagg ctgcaccggt gcgtcagcag aatatgtgat acaggatata ttccgcttcc | 720 |
| tcgctcactg actcgctacg ctcggtcgtt cgactgcggc gagcggaaat ggcttacgaa | 780 |
| cggggcggag atttcctgga agatgccagg aagatactta acaggaagt gagagggccg | 840 |
| cggcaaagcc gttttttcat aggctccgcc ccctgacaa gcatcacgaa atctgacgct | 900 |
| caaatcagtg gtggcgaaac ccgacaggac tataaagata ccaggcgttt ccctggcgg | 960 |
| ctccctcgtg cgctctcctg ttcctgcctt tcggtttacc ggtgtcattc cgctgttatg | 1020 |
| gccgcgtttg tctcattcca cgcctgacac tcagttccgg gtaggcagtt cgctccaagc | 1080 |
| tggactgtat gcacgaaccc cccgttcagt ccgaccgctg cgccttatcc ggtaactatc | 1140 |
| gtcttgagtc aacccggaa agacatgcaa aagcaccact ggcagcagcc actggtaatt | 1200 |
| gatttagagg agttagtctt gaagtcatgc gccggttaag gctaaactga aggacaagt | 1260 |

```
tttggtgact gcgctcctcc aagccagtta cctcggttca aagagttggt agctcagaga    1320
accttcgaaa aaccgccctg caaggcggtt ttttcgtttt cagagcaaga gattacgcgc    1380
agaccaaaac gatctcaaga agatcatctt atgcggccgc atcagataaa atatttctag    1440
atgccgaact cagaagtgaa acgccgtagc gccgatggta gtgtggggtc tccccatgcg    1500
agagtaggga actgccaggc atcaaataaa acgaaaggct cagtcgaaag actgggcctt    1560
tcgttttatc tgttgtttgt cggtgaacgc tctcctgagt aggacaaatc cgccgggagc    1620
ggatttgaac gttgcgaagc aacggcccgg agggtggcgg gcaggacgcc cgccataaac    1680
tgccaggcat caaattaagc agaaggccat cctgacggat ggccttttg cgtttctaca    1740 aactcttcct gtcgtcatat ctacaagcca tcccccgcat gcatgaaacg atggacaccg    1800
aagccatggg tgattaaaga ggccggattg taataattgt acactccgga gtcaattctc    1860
tttccttatt taccgcgctt ttccgcacct tttcgcaggg aaaatgtacg acctcacacc    1920
agtggaaacc agcatggcgc gccgggtgga ggattatacg ggctgatggg taaagcgcaa    1980
ggatcgtcct ggatctttat tagatcgatt aagccaattt ttgtctatgg tcattaaatt    2040
ttccaatatg cggcgtaaat cgtgcccgcc tcgcggcagg atcgtttaca cttagcgagt    2100
tctggaaagt cctgtggata aatcgggaaa atctgtgaga acagaagat ctcttgcgca    2160 gtttaggcta tgatccgcgg tcccgatcgt tttgcaggat cttgatcggg catataaccg    2220
cagacagcgg ttcgtgcgtc accctcaagc agggtctttt cgacgtacgt caacaatcat    2280
gaatgtttca gccttagtca ttatcgactt ttgttcgagt ggagtccgcc gtgtcacttt    2340
cgctttggca gcagtgtctt gcccgattgc aggatgagtt ggtaccgagc tctgagcaac    2400
aagttgtaaa ctcactggct gataaccttg atatccaata tgaagtgtta actaaccatg    2460
gtgctaacga aggtcttgcg tgccaagata tgggcgcaga atgggcttct tgtaacaaag    2520
taaacatgac gcttgttaac caaggtgaag ctgttgactc aaaagattgg gctatttact    2580
tccacagcat tcgtctgatt ctggatgttg acaacgagca gttcaaaatc tctcgtgtaa    2640
cgggtgacct acataagcta gaaccaacag ataagtttga cggcttcgct gccggtgaag    2700
aggttgttct tccattggtt ggtgaatact ggcaactatt tgaaactgac ttcatgccgg    2760
gtgcattcgt ttctgctcca aacgcagaac ctaagatgat tgcttctcta aatactgaag    2820
atgttgcgtc ttttgtgacg ggtcttgaag gtaacaacct aaaacgtaca ccagatgaca    2880
acaatgtatt tgcaaacgct gtgtctcgtt ttgagaaaaa cgaagaccta gcaacacaag    2940
acgtatcaac cacgttacta ccaacaccaa tgcacgttga agcgggtaaa ggcaaagtag    3000
atatcgcgga tggtattgcg ctgcctaaag acgcattcga tgcgactcag ttcgcagcga    3060
ttcaagatcg tgcagaagtg gtaggtgtgg acgttcgtgg tgatcttcct gtaagcatca    3120
ctgttgttcc tgcagacttc accggtgaat tagcaaaatc tggtgcttac gaaatgagca    3180
tcaaaggcga cggtattgtg attaaagcgt tcgaccaagc aggcgctttc tacgcagtac    3240
aatctatctt tggcctggta gatagccaaa atgctgattc tctaccacaa ctgtctatta    3300
aagatgcgcc tcgttttgat taccgtggtg tgatggtgga tgtggctcgt aacttccact    3360
ctaaggacgc aatccttgca acgctagacc aaatggcagc gtacaagatg aacaaacttc    3420
accttcacct aaccgatgat gaaggctggc gtttagaaat cccgggtctg cctgagctga    3480
cagaagtggg tgctaaccgt tgtttcgata cacaagagaa aagctgttta ctgcctcagc    3540
ttggctctgg tccaacgaca gacaactttg gctctggcta cttcagcaaa gcagactacg    3600
tggaaatctt gaaatacgcg aaagcacgta acattgaagt gattccagaa atcgatatgc    3660
```

-continued

```
cagctcacgc tcgtgcagca gtagtatcaa tggaagctcg ttacgaccgc ctaatggaag    3720
aaggtaaaga agctgaagcg aacgaatacc gtctgatgga tcctcaagat acatcaaacg    3780
taacgacggt tcagttctac aataagcaaa gcttcatcaa cccatgtatg gaatcttcaa    3840
ctcgctttgt tgataaggtg atttcagaag tggcagcaat gcaccaagaa gctggcgctc    3900
cactaacaac ttggcacttc ggtggtgacg aagcgaagaa catcaagcta ggtgctggtt    3960
tccaagacgt taacgcagaa gataaagtaa gctggaaagg cacgattgac ctgtctaaac    4020
aagacaagcc gtttgcacag tctccacaat gtcagacgct aatcacagat ggcacagtca    4080
gtgactttgc tcacctacca agccacttcg cggaagaagt gtcgaagatt gttgctgaga    4140
aaggcattcc aaacttccaa gcttggcaag atggtttgaa atacagtgac ggcgaaaaag    4200
cgttcgctac agaaaatact cgcgtaaact tctgggacgt tctgtactgg ggcggtactt    4260
cctcagtgta cgagtggtct aagaaaggtt acgacgtgat tgtttctaac ccagattacg    4320
tgtacatgga tatgccatac gaagttgacc cgaaagagcg tggttactac tgggcaacac    4380
gtgcaacgga tactcgtaag atgtttggct ttgcaccaga gaacatgcct caaaacgcag    4440
aaacttctgt agatcgcgat ggcaatggct ttactggtaa aggtgaaatc gaagcgaaac    4500
ctttctacgg tctatctgca caactttggt ctgagacagt acgtaacgac gagcaatacg    4560
agtacatggt attccctcgc gtcctcgctg ctgctcagcg tgcatggcac cgtgctgact    4620
gggaaaacga ctacaaagtt ggtgttgagt actcgcaaaa ctctaatcta gttgataaag    4680
catcgctaaa ccaagactac aaccgctttg cgaacgtact tggtcaacgt gaactggcta    4740
agctagaaaa atcaggtatt gactaccgcc taccagtacc aggtgcaaaa gtagaagatg    4800
gtaagctagc aatgaacgtt cagttccctg gcgtaacgct tcaatactct ctggatggtg    4860
agaactggtt gactatgca gacaacgctc gtccaaatgt aactggtgaa gtcttcatcc    4920
gctcggtatc tgcgacaggt gagaaggtaa gccgtatcac tagcgtgaaa taatagcgct    4980
cagtattcac taaaatcata gttccttact caaagccctc aacttatgtt gggggctttg    5040
tttatttttc ttcggaaaat aagcgtgatc atgcgacagg tttgatgaca aaaaattagc    5100
gcaagaagac aaaaatcacc ttgcgctaat gctctgttac aggtcactaa taccatctaa    5160
gtagttgatt catagtgact gcatatgttg tgttttacag tattatgtag tctgtttttt    5220
atgcaaaatc taatttaata tattgatatt tatatcattt tacgtttctc gttcagcttt    5280
tttatactaa gttggcatta taaaaaagca ttgcttatca atttgttgca acgaacaggt    5340
cactatcagt caaaataaaa tcattatttg atttcaattt tgtcccactc cctgcctctg    5400
tcatcacgat actgtgatgc catggtgtcc gacttatgcc cgagaagatg ttgagcaaac    5460
ttatcgctta tctgcttctc atagagtctt gcagacaaac tgcgcaactc gtgaaaggta    5520 ggcgccccg tcgaatttg cttcgaatt tctgccattc atccgcttat tatcacttat    5580
tcaggcgtag caccaggcgt ttaagggcac caataactgc cttaaaaaaa ttacgccccg    5640
ccctgccact catcgcagta ctgttgtaat tcattaagca ttctgccgac atggaagcca    5700
tcacagacgg catgatgaac ctgaatcgcc agcggcatca gcaccttgtc gccttgcgta    5760
taatatttgc ccatggtgaa aacgggggcg aagaagttgt ccatattggc cacgtttaaa    5820
tcaaaactgg tgaaactcac ccagggattg gctgagacga aaacatatt ctcaataaac    5880 ccttttaggga aataggccag gttttcaccg taacacgcca catcttgcga atatatgtgt    5940
agaaactgcc ggaaatcgtc gtggtattca ctccagagcg atgaaaacgt ttcagtttgc    6000
```

| | |
|---|---|
| tcatggaaaa cggtgtaaca agggtgaaca ctatcccata tcaccagctc accgtctttc | 6060 |
| attgccatac g | 6071 |

<210> SEQ ID NO 13
<211> LENGTH: 5641
<212> TYPE: DNA
<213> ORGANISM: Artificial Sequence
<220> FEATURE:
<223> OTHER INFORMATION: pJMF3

<400> SEQUENCE: 13

| | |
|---|---|
| gaattccgga tgagcattca tcaggcgggc aagaatgtga ataaaggccg gataaaactt | 60 |
| gtgcttattt ttctttacgg tctttaaaaa ggccgtaata tccagctgaa cggtctggtt | 120 |
| ataggtacat tgagcaactg actgaaatgc ctcaaaatgt tctttacgat gccattggga | 180 |
| tatatcaacg gtggtatatc cagtgatttt tttctccatt ttagcttcct tagctcctga | 240 |
| aaatctcgat aactcaaaaa atacgcccgg tagtgatctt atttcattat ggtgaaagtt | 300 |
| ggaacctctt acgtgccgat caacgtctca ttttcgccaa agttggccc agggcttccc | 360 |
| ggtatcaaca gggacaccag gatttatta tctgcgaag tgatcttccg tcacaggtat | 420 |
| ttattcggcg caaagtgcgt cgggtgatgc tgccaactta ctgatttagt gtatgatggt | 480 |
| gttttttgagg tgctccagtg gcttctgttt ctatcagctg tccctcctgt tcagctactg | 540 |
| acggggtggt gcgtaacggc aaaagcaccg ccggacatca gcgctagcgg agtgtgcggc | 600 |
| cgcactggct tactatgttg gcactgatga gggtgtcagt gaagtgcttc atgtggcagg | 660 |
| agaaaaagg ctgcaccggt gcgtcagcag aatatgtgat acaggatata ttccgcttcc | 720 |
| tcgctcactg actcgctacg ctcggtcgtt cgactgcggc gagcggaaat ggcttacgaa | 780 |
| cggggcggag atttcctgga agatgccagg aagatactta acgggaagt gagagggccg | 840 |
| cggcaaagcc gtttttccat aggctccgcc cccctgacaa gcatcacgaa atctgacgct | 900 |
| caaatcagtg gtggcgaaac ccgacaggac tataaagata ccaggcgttt ccctggcgg | 960 |
| ctccctcgtg cgctctcctg ttcctgcctt tcggtttacc ggtgtcattc cgctgttatg | 1020 |
| gccgcgtttg tctcattcca cgcctgacac tcagttccgg gtaggcagtt cgctccaagc | 1080 |
| tggactgtat gcacgaaccc cccgttcagt ccgaccgctg cgccttatcc ggtaactatc | 1140 |
| gtcttgagtc caacccggaa agacatgcaa aagcaccact ggcagcagcc actggtaatt | 1200 |
| gatttagagg agttagtctt gaagtcatgc gccggttaag ctaaactga aggacaagt | 1260 |
| tttggtgact gcgctcctcc aagccagtta cctcggttca aagagttggt agctcagaga | 1320 |
| accttcgaaa aaccgccctg caaggcggtt ttttcgtttt cagagcaaga gattacgcgc | 1380 |
| agaccaaaac gatctcaaga agatcatctt atgcggccgc atcagataaa atatttctag | 1440 |
| atgccgaact cagaagtgaa acgccgtagc gccgatggta gtgtggggtc tccccatgcg | 1500 |
| agagtaggga actgccaggc atcaaataaa acgaaaggct cagtcgaaag actgggcctt | 1560 |
| tcgttttatc tgttgtttgt cggtgaacgc tctcctgagt aggacaaatc cgccgggagc | 1620 |
| ggatttgaac gttgcgaagc aacggcccgg agggtggcgg gcaggacgcc cgccataaac | 1680 |
| tgccaggcat caaattaagc agaaggccat cctgacggat ggcctttttg cgtttctaca | 1740 |
| aactcttcct gtcgtcatat ctacaagcca tccccgcat gcattaatgt gagttagctc | 1800 |
| actcattagg caccccaggc tttacacttt atgcttccgg ctcgtatgtt gtgtggaatt | 1860 |
| gtgagcggat aacaatttca cacaggaaac agctatgacc atgattacgc caagcttgca | 1920 |
| tgcctgcagg tcgactctag aggatccccg gtaccgagc tctgagcaac aagttgtaaa | 1980 |

-continued

```
ctcactggct gataaccttg atatccaata tgaagtgtta actaaccatg gtgctaacga    2040
aggtcttgcg tgccaagata tgggcgcaga atgggcttct tgtaacaaag taaacatgac    2100
gcttgttaac caaggtgaag ctgttgactc aaaagattgg gctatttact tccacagcat    2160
tcgtctgatt ctggatgttg acaacgagca gttcaaaatc tctcgtgtaa cgggtgacct    2220
acataagcta gaaccaacag ataagtttga cggcttcgct gccggtgaag aggttgttct    2280
tccattggtt ggtgaatact ggcaactatt tgaaactgac ttcatgccgg gtgcattcgt    2340
ttctgctcca aacgcagaac ctaagatgat tgcttctcta atactgaag atgttgcgtc     2400 ttttgtgacg ggtcttgaag gtaacaacct aaaacgtaca ccagatgaca caatgtatt     2460 tgcaaacgct gtgtctcgtt ttgagaaaaa cgaagaccta gcaacacaag acgtatcaac    2520
cacgttacta ccaacaccaa tgcacgttga agcgggtaaa ggcaaagtag atatcgcgga    2580
tggtattgcg ctgcctaaag acgcattcga tgcgactcag ttcgcagcga ttcaagatcg    2640
tgcagaagtg gtaggtgtgg acgttcgtgg tgatcttcct gtaagcatca ctgttgttcc    2700
tgcagacttc accggtgaat tagcaaaatc tggtgcttac gaaatgagca tcaaaggcga    2760
cggtattgtg attaaagcgt tcgaccaagc aggcgctttc tacgcagtac aatctatctt    2820
tggcctggta gatagccaaa atgctgattc tctaccacaa ctgtctatta agatgcgcc     2880 tcgttttgat taccgtggtg tgatggtgga tgtggctcgt aacttccact ctaaggacgc    2940
aatccttgca acgctagacc aaatggcagc gtacaagatg aacaaacttc accttcacct    3000
aaccgatgat gaaggctggc gtttagaaat cccgggtctg cctgagctga cagaagtggg    3060
tgctaaccgt tgtttcgata cacaagagaa aagctgttta ctgcctcagc ttggctctgg    3120
tccaacgaca gacaactttg gctctggcta cttcagcaaa gcagactacg tggaaatctt    3180
gaaatacgcg aaagcacgta acattgaagt gattccagaa atcgatatgc agctcacgc     3240 tcgtgcagca gtagtatcaa tggaagctcg ttacgaccgc ctaatggaag aaggtaaaga    3300
agctgaagcg aacgaatacc gtctgatgga tcctcaagat acatcaaacg taacgacggt    3360
tcagttctac aataagcaaa gcttcatcaa cccatgtatg gaatcttcaa ctcgcttttgt   3420 tgataaggtg atttcagaag tggcagcaat gcaccaagaa gctggcgctc cactaacaac    3480
ttggcacttc ggtggtgacg aagcgaagaa catcaagcta ggtgctggtt tccaagacgt    3540
taacgcagaa gataaagtaa gctggaaagg cacgattgac ctgtctaaac aagacaagcc    3600
gtttgcacag tctccacaat gtcagacgct aatcacagat ggcacagtca gtgactttgc    3660
tcacctacca agccacttcg cggaagaagt gtcgaagatt gttgctgaga aaggcattcc    3720
aaacttccaa gcttggcaag atggtttgaa atacagtgac ggcgaaaaag cgttcgctac    3780
agaaaatact cgcgtaaact tctgggacgt tctgtactgg ggcggtactt cctcagtgta    3840
cgagtggtct aagaaaggtt acgacgtgat tgtttctaac ccagattacg tgtacatgga    3900
tatgccatac gaagttgacc cgaaagagcg tggttactac tgggcaacac gtgcaacgga    3960
tactcgtaag atgtttggct ttgcaccaga gaacatgcct caaaacgcag aaacttctgt    4020
agatcgcgat ggcaatggct ttactggtaa aggtgaaatc gaagcgaaac ctttctacgg    4080
tctatctgca caactttggt ctgagacagt acgtaacgac gagcaatacg agtacatggt    4140
attccctcgc gtcctcgctg ctgctcagcg tgcatggcac cgtgctgact gggaaaacga    4200
ctacaaagtt ggtgttgagt actcgcaaaa ctctaatcta gttgataaag catcgctaaa    4260
ccaagactac aaccgctttg cgaacgtact tggtcaacgt gaactggcta agctagaaaa    4320
```

```
atcaggtatt gactaccgcc taccagtacc aggtgcaaaa gtagaagatg gtaagctagc    4380
aatgaacgtt cagttccctg gcgtaacgct tcaatactct ctggatggtg agaactggtt    4440
gacttatgca gacaacgctc gtccaaatgt aactggtgaa gtcttcatcc gctcggtatc    4500
tgcgacaggt gagaaggtaa gccgtatcac tagcgtgaaa taatagcgct cagtattcac    4560
taaaatcata gttccttact caaagccctc aacttatgtt gggggctttg tttatttttc    4620
ttcggaaaat aagcgtgatc atgcgacagg tttgatgaca aaaaattagc gcaagaagac    4680
aaaaatcacc ttgcgctaat gctctgttac aggtcactaa taccatctaa gtagttgatt    4740
catagtgact gcatatgttg tgttttacag tattatgtag tctgtttttt atgcaaaatc    4800
taatttaata tattgatatt tatatcattt tacgtttctc gttcagcttt tttatactaa    4860
gttggcatta taaaaaagca ttgcttatca atttgttgca acgaacaggt cactatcagt    4920
caaaataaaa tcattatttg atttcaattt tgtcccactc cctgcctctg tcatcacgat    4980
actgtgatgc catggtgtcc gacttatgcc cgagaagatg ttgagcaaac ttatcgctta    5040
tctgcttctc atagagtctt gcagacaaac tgcgcaactc gtgaaaggta ggcgcccccg    5100
gtcgaatttg ctttcgaatt tctgccattc atccgcttat tatcacttat tcaggcgtag    5160
caccaggcgt ttaagggcac caataactgc cttaaaaaaa ttacgccccg ccctgccact    5220
catcgcagta ctgttgtaat tcattaagca ttctgccgac atggaagcca tcacagacgg    5280
catgatgaac ctgaatcgcc agcggcatca gcaccttgtc gccttgcgta taatatttgc    5340
ccatggtgaa acgggggcg aagaagttgt ccatattggc cacgtttaaa tcaaaactgg    5400
tgaaactcac ccagggattg gctgagacga aaacatatt ctcaataaac cctttaggga    5460
aataggccag ttttcaccg taacacgcca catcttgcga atatatgtgt agaaactgcc    5520
ggaaatcgtc gtggtattca ctccagagcg atgaaaacgt ttcagtttgc tcatggaaaa    5580
cggtgtaaca agggtgaaca ctatcccata tcaccagctc accgtctttc attgccatac    5640
g                                                                   5641

<210> SEQ ID NO 14
<211> LENGTH: 5670
<212> TYPE: DNA
<213> ORGANISM: Artificial Sequence
<220> FEATURE:
<223> OTHER INFORMATION: pJMF4

<400> SEQUENCE: 14
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa agttggccc agggcttccc    360 ggtatcaaca gggacaccag gatttattta ttctgcgaag tgatcttccg tcacaggtat    420
ttattcggcg caaagtgcgt cgggtgatgc tgccaactta ctgatttagt gtatgatggt    480 gttttttgagg tgctccagtg gcttctgttt ctatcagctg tccctcctgt tcagctactg    540
acggggtggt gcgtaacggc aaaagcaccg ccggacatca gcgctagcgg agtgtgcggc    600
cgcactggct tactatgttg gcactgatga gggtgtcagt gaagtgcttc atgtggcagg    660
agaaaaaagg ctgcaccggt gcgtcagcag aatatgtgat acaggatata ttccgcttcc    720
```

-continued

```
tcgctcactg actcgctacg ctcggtcgtt cgactgcggc gagcggaaat ggcttacgaa     780
cggggcggag atttcctgga agatgccagg aagatactta acagggaagt gagagggccg     840
cggcaaagcc gttttccat aggctccgcc ccctgacaa gcatcacgaa atctgacgct       900
caaatcagtg gtggcgaaac ccgacaggac tataaagata ccaggcgttt ccctggcgg      960
ctccctcgtg cgctctcctg ttcctgcctt tcggtttacc ggtgtcattc cgctgttatg    1020
gccgcgtttg tctcattcca cgcctgacac tcagttccgg gtaggcagtt cgctccaagc    1080
tggactgtat gcacgaaccc cccgttcagt ccgaccgctg cgccttatcc ggtaactatc    1140
gtcttgagtc aacccggaa agacatgcaa aagcaccact ggcagcagcc actggtaatt     1200
gatttagagg agttagtctt gaagtcatgc gccggttaag gctaaactga aggacaagt     1260
tttggtgact gcgctcctcc aagccagtta cctcggttca aagagttggt agctcagaga    1320
accttcgaaa accgccctg caaggcggtt ttttcgtttt cagagcaaga gattacgcgc     1380
agaccaaaac gatctcaaga agatcatctt atgcggccgc atcagataaa atatttctag    1440
atgccgaact cagaagtgaa acgccgtagc gccgatggta gtgtgggtc tccccatgcg     1500
agagtaggga actgccaggc atcaaataaa acgaaaggct cagtcgaaag actgggcctt    1560
tcgttttatc tgttgtttgt cggtgaacgc tctcctgagt aggacaaatc cgccgggagc    1620
ggatttgaac gttgcgaagc aacggcccgg agggtggcgg gcaggacgcc cgccataaac    1680
tgccaggcat caaattaagc agaaggccat cctgacggat ggcctttttg cgtttctaca    1740
aactcttcct gtcgtcatat ctacaagcca tcccccgcat gcattaatgt gagttagctc    1800
actcattagg caccccaggc tttacacttt atgcttccgg ctcgtatgtt gtgtggaatt    1860
gtgagcggat aacaatttca cacaggaaac agctatgacc atgattacgc caagcttgca    1920
tgcctgcagg tcgactctag aggatccccg ggtaccgagc tctgagcaac aagttgtaaa    1980
ctcactggct gataaccttg atatccaata tgaagtgtta actaaccatg gtgctaacga    2040
aggtcttgcg tgccaagata tgggcgcaga atgggcttct tgtaacaaag taaacatgac    2100
gcttgttaac caaggtgaag ctgttgactc aaaagattgg gctatttact tccacagcat    2160
tcgtctgatt ctggatgttg acaacgagca gttcaaaatc tctcgtgtaa cgggtgacct    2220
acataagcta gaaccaacag ataagtttga cggcttcgct gccggtgaag aggttgttct    2280
tccattggtt ggtgaatact ggcaactatt tgaaactgac ttcatgccgg gtgcattcgt    2340
ttctgctcca aacgcagaac ctaagatgat tgcttctcta aatactgaag atgttgcgtc    2400
ttttgtgacg ggtcttgaag gtaacaacct aaaacgtaca ccagatgaca caatgtatt    2460
tgcaaacgct gtgtctcgtt ttgagaaaaa cgaagaccta gcaacacaag acgtatcaac    2520
cacgttacta ccaacaccaa tgcacgttga agcgggtaaa ggcaaagtag atatcgcgga    2580
tggtattgcg ctgcctaaag acgcattcga tgcgactcag ttcgcagcga ttcaagatcg    2640
tgcagaagtg gtaggtgtgg acgttcgtgg tgatcttcct gtaagcatca ctgttgttcc    2700
tgcagacttc accggtgaat tagcaaaatc tggtgcttac gaaatgagca tcaaaggcga    2760
cggtattgtg attaaagcgt tcgaccaagc aggcgctttc tacgcagtac aatctatctt    2820
tggcctggta gatagccaaa atgctgattc tctaccacaa ctgtctatta agatgcgcc     2880
tcgttttgat taccgtggtg tgatggtgga tgtggctcgt aacttccact ctaaggacgc    2940
aatccttgca acgctagacc aaatggcagc gtacaagatg aacaaacttc accttcacct    3000
aaccgatgat gaaggctggc gtttagaaat cccgggtctg cctgagctga cagaagtggg    3060
```

```
tgctaaccgt tgtttcgata cacaagagaa aagctgttta ctgcctcagc ttggctctgg    3120
tccaacgaca gacaactttg gctctggcta cttcagcaaa gcagactacg tggaaatctt    3180
gaaatacgcg aaagcacgta acattgaagt gattccagaa atcgatatgc cagctcacgc    3240
tcgtgcagca gtagtatcaa tggaagctcg ttacgaccgc ctaatggaag aaggtaaaga    3300
agctgaagcg aacgaatacc gtctgatgga tcctcaagat acatcaaacg taacgacggt    3360
tcagttctac aataagcaaa gcttcatcaa cccatgtatg gaatcttcaa ctcgctttgt    3420
tgataaggtg atttcagaag tggcagcaat gcaccaagaa gctggcgctc cactaacaac    3480
ttggcacttc ggtggtgacg aagcgaagaa catcaagcta ggtgctggtt ccaagacgt    3540 taacgcagaa gataaagtaa gctggaaagg cacgattgac ctgtctaaac aagacaagcc    3600 gttttgcacag tctccacaat gtcagacgct aatcacagat ggcacagtca gtgactttgc    3660
tcacctacca agccacttcg cggaagaagt gtcgaagatt gttgctgaga aaggcattcc    3720
aaacttccaa gcttggcaag atggtttgaa atacagtgac ggcgaaaaag cgttcgctac    3780
agaaaatact cgcgtaaact ctgggacgt tctgtactgg ggcggtactt cctcagtgta    3840
cgagtggtct aagaaaggtt acgacgtgat tgtttctaac ccagattacg tgtacatgga    3900
tatgccatac gaagttgacc cgaaagagcg tggttactac tgggcaacac gtgcaacgga    3960
tactcgtaag atgtttggct ttgcaccaga gaacatgcct caaaacgcag aaacttctgt    4020
agatcgcgat ggcaatggct ttactggtaa aggtgaaatc gaagcgaaac ctttctacgg    4080
tctatctgca caactttggt ctgagacagt acgtaacgac gagcaatacg agtacatggt    4140
attccctcgc gtcctcgctg ctgctcagcg tgcatggcac cgtgctgact gggaaaacga    4200
ctacaaagtt ggtgttgagt actcgcaaaa ctctaatcta gttgataaag catcgctaaa    4260
ccaagactac aaccgctttg cgaacgtact tggtcaacgt gaactggcta agctagaaaa    4320
atcaggtatt gactaccgcc taccagtacc aggtgcaaaa gtagaagatg gtaagctagc    4380
aatgaacgtt cagttccctg gcgtaacgct tcaatactct ctggatggtg agaactggtt    4440
gacttatgca gacaacgctc gtccaaatgt aactggtgaa gtcttcatcc gctcggtatc    4500
tgcgacaggt gagaaggtaa gccgtatcac tagcgtgaaa taatagcgct cagtattcac    4560
taaaatcata gttccttact caaagccctc aacttatgtt gggggctttg tttatttttc    4620
ttcggaaaat aagcgtgatc ccccggggc gcctaccttt cacgagttgc gcagtttgtc    4680
tgcaagactc tatgagaagc agataagcga taagtttgct caacatcttc tcgggcataa    4740
gtcggacacc atggcatcac agtatcgtga tgacagaggc agggagtggg acaaaattga    4800
aatcaaataa tgattttatt ttgactgata gtgacctgtt cgttgcaaca aattgataag    4860
caatgctttt ttataatgcc aacttagtat aaaaaagctg aacgagaaac gtaaaatgat    4920
ataaatatca atatattaaa ttagattttg cataaaaaac agactacata atactgtaaa    4980
acacaacata tgcagtcact atgaatcaac tacttagatg gtattagtga cctgtaacag    5040
agcattagcg caaggtgatt tttgtcttct tgcgctaatt ttttgtcatc aaacctgtcg    5100
catgatcatg gggctgcagg aattcgatgg tcgaatttgc tttcgaattt ctgccattca    5160
tccgcttatt atcacttatt caggcgtagc accaggcgtt taagggcacc ataactgcc    5220 ttaaaaaaat tacgccccgc cctgccactc atcgcagtac tgttgtaatt cattaagcat    5280
tctgccgaca tggaagccat cacagacggc atgatgaacc tgaatcgcca gcggcatcag    5340
caccttgtcg ccttgcgtat aatatttgcc catggtgaaa acgggggcga agaagttgtc    5400
catattggcc acgtttaaat caaaactggt gaaactcacc cagggattgg ctgagacgaa    5460
```

```
aaacatattc tcaataaacc ctttagggaa ataggccagg ttttcaccgt aacacgccac    5520
atcttgcgaa tatatgtgta gaaactgccg gaaatcgtcg tggtattcac tccagagcga    5580
tgaaaacgtt tcagtttgct catggaaaac ggtgtaacaa gggtgaacac tatcccatat    5640
caccagctca ccgtctttca ttgccatacg                                    5670
```

<210> SEQ ID NO 15
<211> LENGTH: 238
<212> TYPE: DNA
<213> ORGANISM: Artificial Sequence
<220> FEATURE:
<223> OTHER INFORMATION: LacZ(/chitobiase Fusion
<221> NAME/KEY: CDS
<222> LOCATION: (119)...(238)
<221> NAME/KEY: -35_signal
<222> LOCATION: (44)...(50)
<223> OTHER INFORMATION: Lac promoter
<221> NAME/KEY: -10_signal
<222> LOCATION: (69)...(74)
<223> OTHER INFORMATION: Lac promoter
<221> NAME/KEY: protein_bind
<222> LOCATION: (81)...(107)
<223> OTHER INFORMATION: Lac repressor binding site
<221> NAME/KEY: protein_bind
<222> LOCATION: (7)...(34)
<223> OTHER INFORMATION: CAP-cAMP binding site

<400> SEQUENCE: 15

```
gcatgcatta atgtgagtta gctcactcat taggcacccc aggctttaca ctttatgctt     60
ccggctcgta tgttgtgtgg aattgtgagc ggataacaat ttcacacagg aaacagct     118 atg acc atg att acg cca agc ttg cat gcc tgc agg tcg act cta gag    166
Met Thr Met Ile Thr Pro Ser Leu His Ala Cys Arg Ser Thr Leu Glu
 1               5                  10                  15 gat ccc cgg gta ccg agc tct gag caa caa gtt gta aac tca ctg gct    214
Asp Pro Arg Val Pro Ser Ser Glu Gln Gln Val Val Asn Ser Leu Ala
             20                  25                  30 gat aac ctt gat atc caa tat gaa                                     238
Asp Asn Leu Asp Ile Gln Tyr Glu
         35                  40
```

<210> SEQ ID NO 16
<211> LENGTH: 40
<212> TYPE: PRT
<213> ORGANISM: Artificial Sequence
<220> FEATURE:
<223> OTHER INFORMATION: LacZ(/chitobiase Fusion

<400> SEQUENCE: 16

```
Met Thr Met Ile Thr Pro Ser Leu His Ala Cys Arg Ser Thr Leu Glu
 1               5                  10                  15

Asp Pro Arg Val Pro Ser Ser Glu Gln Gln Val Val Asn Ser Leu Ala
             20                  25                  30

Asp Asn Leu Asp Ile Gln Tyr Glu
         35                  40
```

<210> SEQ ID NO 17
<211> LENGTH: 22
<212> TYPE: PRT
<213> ORGANISM: Artificial Sequence
<220> FEATURE:
<223> OTHER INFORMATION: dnaA/chitobiase Fusion

<400> SEQUENCE: 17

```
Met Ser Leu Ser Leu Trp Gln Gln Cys Leu Ala Arg Leu Gln Asp Glu
```

<210> SEQ ID NO 18
<211> LENGTH: 2643
<212> TYPE: DNA
<213> ORGANISM: Artificial Sequence
<220> FEATURE:
<221> NAME/KEY: CDS
<222> LOCATION: (1)...(2643)
<223> OTHER INFORMATION: dnaA/Chitobiase Fusion

<400> SEQUENCE: 18

```
gtg tca ctt tcg ctt tgg cag cag tgt ctt gcc cga ttg cag gat gag      48
Met Ser Leu Ser Leu Trp Gln Gln Cys Leu Ala Arg Leu Gln Asp Glu
 1               5                  10                  15 ttg gta ccg agc tct gag caa caa gtt gta aac tca ctg gct gat aac      96
Leu Val Pro Ser Ser Glu Gln Gln Val Val Asn Ser Leu Ala Asp Asn
             20                  25                  30 ctt gat atc caa tat gaa gtg tta act aac cat ggt gct aac gaa ggt     144
Leu Asp Ile Gln Tyr Glu Val Leu Thr Asn His Gly Ala Asn Glu Gly
         35                  40                  45 ctt gcg tgc caa gat atg ggc gca gaa tgg gct tct tgt aac aaa gta     192
Leu Ala Cys Gln Asp Met Gly Ala Glu Trp Ala Ser Cys Asn Lys Val
     50                  55                  60 aac atg acg ctt gtt aac caa ggt gaa gct gtt gac tca aaa gat tgg     240
Asn Met Thr Leu Val Asn Gln Gly Glu Ala Val Asp Ser Lys Asp Trp
 65                  70                  75                  80 gct att tac ttc cac agc att cgt ctg att ctg gat gtt gac aac gag     288
Ala Ile Tyr Phe His Ser Ile Arg Leu Ile Leu Asp Val Asp Asn Glu
                 85                  90                  95 cag ttc aaa atc tct cgt gta acg ggt gac cta cat aag cta gaa cca     336
Gln Phe Lys Ile Ser Arg Val Thr Gly Asp Leu His Lys Leu Glu Pro
            100                 105                 110 aca gat aag ttt gac ggc ttc gct gcc ggt gaa gag gtt gtt ctt cca     384
Thr Asp Lys Phe Asp Gly Phe Ala Ala Gly Glu Glu Val Val Leu Pro
        115                 120                 125 ttg gtt ggt gaa tac tgg caa cta ttt gaa act gac ttc atg ccg ggt     432
Leu Val Gly Glu Tyr Trp Gln Leu Phe Glu Thr Asp Phe Met Pro Gly
    130                 135                 140 gca ttc gtt tct gct cca aac gca gaa cct aag atg att gct tct cta     480
Ala Phe Val Ser Ala Pro Asn Ala Glu Pro Lys Met Ile Ala Ser Leu
145                 150                 155                 160 aat act gaa gat gtt gcg tct ttt gtg acg ggt ctt gaa ggt aac aac     528
Asn Thr Glu Asp Val Ala Ser Phe Val Thr Gly Leu Glu Gly Asn Asn
                165                 170                 175 cta aaa cgt aca cca gat gac aac aat gta ttt gca aac gct gtg tct     576
Leu Lys Arg Thr Pro Asp Asp Asn Asn Val Phe Ala Asn Ala Val Ser
            180                 185                 190 cgt ttt gag aaa aac gaa gac cta gca aca caa gac gta tca acc acg     624
Arg Phe Glu Lys Asn Glu Asp Leu Ala Thr Gln Asp Val Ser Thr Thr
        195                 200                 205 tta cta cca aca cca atg cac gtt gaa gcg ggt aaa ggc aaa gta gat     672
Leu Leu Pro Thr Pro Met His Val Glu Ala Gly Lys Gly Lys Val Asp
    210                 215                 220 atc gcg gat ggt att gcg ctg cct aaa gac gca ttc gat gcg act cag     720
Ile Ala Asp Gly Ile Ala Leu Pro Lys Asp Ala Phe Asp Ala Thr Gln
225                 230                 235                 240 ttc gca gcg att caa gat cgt gca gaa gtg gta ggt gtg gac gtt cgt     768
Phe Ala Ala Ile Gln Asp Arg Ala Glu Val Val Gly Val Asp Val Arg
```

```
                245                 250                 255
ggt gat ctt cct gta agc atc act gtt gtt cct gca gac ttc acc ggt       816
Gly Asp Leu Pro Val Ser Ile Thr Val Val Pro Ala Asp Phe Thr Gly
            260                 265                 270 gaa tta gca aaa tct ggt gct tac gaa atg agc atc aaa ggc gac ggt       864
Glu Leu Ala Lys Ser Gly Ala Tyr Glu Met Ser Ile Lys Gly Asp Gly
            275                 280                 285 att gtg att aaa gcg ttc gac caa gca ggc gct ttc tac gca gta caa       912
Ile Val Ile Lys Ala Phe Asp Gln Ala Gly Ala Phe Tyr Ala Val Gln
            290                 295                 300 tct atc ttt ggc ctg gta gat agc caa aat gct gat tct cta cca caa       960
Ser Ile Phe Gly Leu Val Asp Ser Gln Asn Ala Asp Ser Leu Pro Gln
305                 310                 315                 320 ctg tct att aaa gat gcg cct cgt ttt gat tac cgt ggt gtg atg gtg      1008
Leu Ser Ile Lys Asp Ala Pro Arg Phe Asp Tyr Arg Gly Val Met Val
            325                 330                 335 gat gtg gct cgt aac ttc cac tct aag gac gca atc ctt gca acg cta      1056
Asp Val Ala Arg Asn Phe His Ser Lys Asp Ala Ile Leu Ala Thr Leu
            340                 345                 350 gac caa atg gca gcg tac aag atg aac aaa ctt cac ctt cac cta acc      1104
Asp Gln Met Ala Ala Tyr Lys Met Asn Lys Leu His Leu His Leu Thr
            355                 360                 365 gat gat gaa ggc tgg cgt tta gaa atc ccg ggt ctg cct gag ctg aca      1152
Asp Asp Glu Gly Trp Arg Leu Glu Ile Pro Gly Leu Pro Glu Leu Thr
370                 375                 380 gaa gtg ggt gct aac cgt tgt ttc gat aca caa gag aaa agc tgt tta      1200
Glu Val Gly Ala Asn Arg Cys Phe Asp Thr Gln Glu Lys Ser Cys Leu
385                 390                 395                 400 ctg cct cag ctt ggc tct ggt cca acg aca gac aac ttt ggc tct ggc      1248
Leu Pro Gln Leu Gly Ser Gly Pro Thr Thr Asp Asn Phe Gly Ser Gly
            405                 410                 415 tac ttc agc aaa gca gac tac gtg gaa atc ttg aaa tac gcg aaa gca      1296
Tyr Phe Ser Lys Ala Asp Tyr Val Glu Ile Leu Lys Tyr Ala Lys Ala
            420                 425                 430 cgt aac att gaa gtg att cca gaa atc gat atg cca gct cac gct cgt      1344
Arg Asn Ile Glu Val Ile Pro Glu Ile Asp Met Pro Ala His Ala Arg
            435                 440                 445 gca gca gta gta tca atg gaa gct cgt tac gac cgc cta atg gaa gaa      1392
Ala Ala Val Val Ser Met Glu Ala Arg Tyr Asp Arg Leu Met Glu Glu
450                 455                 460 ggt aaa gaa gct gaa gcg aac gaa tac cgt ctg atg gat cct caa gat      1440
Gly Lys Glu Ala Glu Ala Asn Glu Tyr Arg Leu Met Asp Pro Gln Asp
465                 470                 475                 480 aca tca aac gta acg acg gtt cag ttc tac aat aag caa agc ttc atc      1488
Thr Ser Asn Val Thr Thr Val Gln Phe Tyr Asn Lys Gln Ser Phe Ile
            485                 490                 495 aac cca tgt atg gaa tct tca act cgc ttt gtt gat aag gtg att tca      1536
Asn Pro Cys Met Glu Ser Ser Thr Arg Phe Val Asp Lys Val Ile Ser
            500                 505                 510 gaa gtg gca gca atg cac caa gaa gct ggc gct cca cta aca act tgg      1584
Glu Val Ala Ala Met His Gln Glu Ala Gly Ala Pro Leu Thr Thr Trp
            515                 520                 525 cac ttc ggt ggt gac gaa gcg aag aac atc aag cta ggt gct ggt ttc      1632
His Phe Gly Gly Asp Glu Ala Lys Asn Ile Lys Leu Gly Ala Gly Phe
            530                 535                 540 caa gac gtt aac gca gaa gat aaa gta agc tgg aaa ggc acg att gac      1680
Gln Asp Val Asn Ala Glu Asp Lys Val Ser Trp Lys Gly Thr Ile Asp
545                 550                 555                 560 ctg tct aaa caa gac aag ccg ttt gca cag tct cca caa tgt cag acg      1728
```

```
                                                              -continued

Leu Ser Lys Gln Asp Lys Pro Phe Ala Gln Ser Pro Gln Cys Gln Thr
                565             570                 575 cta atc aca gat ggc aca gtc agt gac ttt gct cac cta cca agc cac      1776
Leu Ile Thr Asp Gly Thr Val Ser Asp Phe Ala His Leu Pro Ser His
            580                 585                 590 ttc gcg gaa gaa gtg tcg aag att gtt gct gag aaa ggc att cca aac      1824
Phe Ala Glu Glu Val Ser Lys Ile Val Ala Glu Lys Gly Ile Pro Asn
        595                 600                 605 ttc caa gct tgg caa gat ggt ttg aaa tac agt gac ggc gaa aaa gcg      1872
Phe Gln Ala Trp Gln Asp Gly Leu Lys Tyr Ser Asp Gly Glu Lys Ala
    610                 615                 620 ttc gct aca gaa aat act cgc gta aac ttc tgg gac gtt ctg tac tgg      1920
Phe Ala Thr Glu Asn Thr Arg Val Asn Phe Trp Asp Val Leu Tyr Trp
625                 630                 635                 640 ggc ggt act tcc tca gtg tac gag tgg tct aag aaa ggt tac gac gtg      1968
Gly Gly Thr Ser Ser Val Tyr Glu Trp Ser Lys Lys Gly Tyr Asp Val
                645                 650                 655 att gtt tct aac cca gat tac gtg tac atg gat atg cca tac gaa gtt      2016
Ile Val Ser Asn Pro Asp Tyr Val Tyr Met Asp Met Pro Tyr Glu Val
            660                 665                 670 gac ccg aaa gag cgt ggt tac tac tgg gca aca cgt gca acg gat act      2064
Asp Pro Lys Glu Arg Gly Tyr Tyr Trp Ala Thr Arg Ala Thr Asp Thr
        675                 680                 685 cgt aag atg ttt ggc ttt gca cca gag aac atg cct caa aac gca gaa      2112
Arg Lys Met Phe Gly Phe Ala Pro Glu Asn Met Pro Gln Asn Ala Glu
    690                 695                 700 act tct gta gat cgc gat ggc aat ggc ttt act ggt aaa ggt gaa atc      2160
Thr Ser Val Asp Arg Asp Gly Asn Gly Phe Thr Gly Lys Gly Glu Ile
705                 710                 715                 720 gaa gcg aaa cct ttc tac ggt cta tct gca caa ctt tgg tct gag aca      2208
Glu Ala Lys Pro Phe Tyr Gly Leu Ser Ala Gln Leu Trp Ser Glu Thr
                725                 730                 735 gta cgt aac gac gag caa tac gag tac atg gta ttc cct cgc gtc ctc      2256
Val Arg Asn Asp Glu Gln Tyr Glu Tyr Met Val Phe Pro Arg Val Leu
            740                 745                 750 gct gct gct cag cgt gca tgg cac cgt gct gac tgg gaa aac gac tac      2304
Ala Ala Ala Gln Arg Ala Trp His Arg Ala Asp Trp Glu Asn Asp Tyr
        755                 760                 765 aaa gtt ggt gtt gag tac tcg caa aac tct aat cta gtt gat aaa gca      2352
Lys Val Gly Val Glu Tyr Ser Gln Asn Ser Asn Leu Val Asp Lys Ala
    770                 775                 780 tcg cta aac caa gac tac aac cgc ttt gcg aac gta ctt ggt caa cgt      2400
Ser Leu Asn Gln Asp Tyr Asn Arg Phe Ala Asn Val Leu Gly Gln Arg
785                 790                 795                 800 gaa ctg gct aag cta gaa aaa tca ggt att gac tac cgc cta cca gta      2448
Glu Leu Ala Lys Leu Glu Lys Ser Gly Ile Asp Tyr Arg Leu Pro Val
                805                 810                 815 cca ggt gca aaa gta gaa gat ggt aag cta gca atg aac gtt cag ttc      2496
Pro Gly Ala Lys Val Glu Asp Gly Lys Leu Ala Met Asn Val Gln Phe
            820                 825                 830 cct ggc gta acg ctt caa tac tct ctg gat ggt gag aac tgg ttg act      2544
Pro Gly Val Thr Leu Gln Tyr Ser Leu Asp Gly Glu Asn Trp Leu Thr
        835                 840                 845 tat gca gac aac gct cgt cca aat gta act ggt gaa gtc ttc atc cgc      2592
Tyr Ala Asp Asn Ala Arg Pro Asn Val Thr Gly Glu Val Phe Ile Arg
    850                 855                 860 tcg gta tct gcg aca ggt gag aag gta agc cgt atc act agc gtg aaa      2640
Ser Val Ser Ala Thr Gly Glu Lys Val Ser Arg Ile Thr Ser Val Lys
865                 870                 875                 880
```

-continued

```
taa                                                                    2643
 *
```

<210> SEQ ID NO 19
<211> LENGTH: 880
<212> TYPE: PRT
<213> ORGANISM: Artificial Sequence
<220> FEATURE:
<223> OTHER INFORMATION: dnaA/Chitobiase Fusion

<400> SEQUENCE: 19

```
Met Ser Leu Ser Leu Trp Gln Gln Cys Leu Ala Arg Leu Gln Asp Glu
 1               5                  10                  15

Leu Val Pro Ser Ser Glu Gln Gln Val Val Asn Ser Leu Ala Asp Asn
            20                  25                  30

Leu Asp Ile Gln Tyr Glu Val Leu Thr Asn His Gly Ala Asn Glu Gly
        35                  40                  45

Leu Ala Cys Gln Asp Met Gly Ala Glu Trp Ala Ser Cys Asn Lys Val
    50                  55                  60

Asn Met Thr Leu Val Asn Gln Gly Glu Ala Val Asp Ser Lys Asp Trp
65                  70                  75                  80

Ala Ile Tyr Phe His Ser Ile Arg Leu Ile Leu Asp Val Asp Asn Glu
                85                  90                  95

Gln Phe Lys Ile Ser Arg Val Thr Gly Asp Leu His Lys Leu Glu Pro
           100                 105                 110

Thr Asp Lys Phe Asp Gly Phe Ala Ala Gly Glu Glu Val Val Leu Pro
       115                 120                 125

Leu Val Gly Glu Tyr Trp Gln Leu Phe Glu Thr Asp Phe Met Pro Gly
   130                 135                 140

Ala Phe Val Ser Ala Pro Asn Ala Glu Pro Lys Met Ile Ala Ser Leu
145                 150                 155                 160

Asn Thr Glu Asp Val Ala Ser Phe Val Thr Gly Leu Glu Gly Asn Asn
               165                 170                 175

Leu Lys Arg Thr Pro Asp Asp Asn Val Phe Ala Asn Ala Val Ser
           180                 185                 190

Arg Phe Glu Lys Asn Glu Asp Leu Ala Thr Gln Asp Val Ser Thr Thr
       195                 200                 205

Leu Leu Pro Thr Pro Met His Val Glu Ala Gly Lys Gly Lys Val Asp
   210                 215                 220

Ile Ala Asp Gly Ile Ala Leu Pro Lys Asp Ala Phe Asp Ala Thr Gln
225                 230                 235                 240

Phe Ala Ala Ile Gln Asp Arg Ala Glu Val Val Gly Val Asp Val Arg
               245                 250                 255

Gly Asp Leu Pro Val Ser Ile Thr Val Val Pro Ala Asp Phe Thr Gly
           260                 265                 270

Glu Leu Ala Lys Ser Gly Ala Tyr Glu Met Ser Ile Lys Gly Asp Gly
       275                 280                 285

Ile Val Ile Lys Ala Phe Asp Gln Ala Gly Ala Phe Tyr Ala Val Gln
   290                 295                 300

Ser Ile Phe Gly Leu Val Asp Ser Gln Asn Ala Asp Ser Leu Pro Gln
305                 310                 315                 320

Leu Ser Ile Lys Asp Ala Pro Arg Phe Asp Tyr Arg Gly Val Met Val
               325                 330                 335

Asp Val Ala Arg Asn Phe His Ser Lys Asp Ala Ile Leu Ala Thr Leu
           340                 345                 350
```

-continued

```
Asp Gln Met Ala Ala Tyr Lys Met Asn Lys Leu His Leu His Leu Thr
        355                 360                 365
Asp Asp Glu Gly Trp Arg Leu Glu Ile Pro Gly Leu Pro Glu Leu Thr
        370                 375                 380
Glu Val Gly Ala Asn Arg Cys Phe Asp Thr Gln Glu Lys Ser Cys Leu
385                 390                 395                 400
Leu Pro Gln Leu Gly Ser Gly Pro Thr Thr Asp Asn Phe Gly Ser Gly
                405                 410                 415
Tyr Phe Ser Lys Ala Asp Tyr Val Glu Ile Leu Lys Tyr Ala Lys Ala
                420                 425                 430
Arg Asn Ile Glu Val Ile Pro Glu Ile Asp Met Pro Ala His Ala Arg
                435                 440                 445
Ala Ala Val Val Ser Met Glu Ala Arg Tyr Asp Arg Leu Met Glu Glu
        450                 455                 460
Gly Lys Glu Ala Glu Ala Asn Glu Tyr Arg Leu Met Asp Pro Gln Asp
465                 470                 475                 480
Thr Ser Asn Val Thr Thr Val Gln Phe Tyr Asn Lys Gln Ser Phe Ile
                485                 490                 495
Asn Pro Cys Met Glu Ser Ser Thr Arg Phe Val Asp Lys Val Ile Ser
                500                 505                 510
Glu Val Ala Ala Met His Gln Glu Ala Gly Ala Pro Leu Thr Thr Trp
        515                 520                 525
His Phe Gly Gly Asp Glu Ala Lys Asn Ile Lys Leu Gly Ala Gly Phe
        530                 535                 540
Gln Asp Val Asn Ala Glu Asp Lys Val Ser Trp Lys Gly Thr Ile Asp
545                 550                 555                 560
Leu Ser Lys Gln Asp Lys Pro Phe Ala Gln Ser Pro Gln Cys Gln Thr
                565                 570                 575
Leu Ile Thr Asp Gly Thr Val Ser Asp Phe Ala His Leu Pro Ser His
                580                 585                 590
Phe Ala Glu Glu Val Ser Lys Ile Val Ala Glu Lys Gly Ile Pro Asn
        595                 600                 605
Phe Gln Ala Trp Gln Asp Gly Leu Lys Tyr Ser Asp Gly Glu Lys Ala
        610                 615                 620
Phe Ala Thr Glu Asn Thr Arg Val Asn Phe Trp Asp Val Leu Tyr Trp
625                 630                 635                 640
Gly Gly Thr Ser Ser Val Tyr Glu Trp Ser Lys Lys Gly Tyr Asp Val
                645                 650                 655
Ile Val Ser Asn Pro Asp Tyr Val Tyr Met Asp Met Pro Tyr Glu Val
                660                 665                 670
Asp Pro Lys Glu Arg Gly Tyr Tyr Trp Ala Thr Arg Ala Thr Asp Thr
                675                 680                 685
Arg Lys Met Phe Gly Phe Ala Pro Glu Asn Met Pro Gln Asn Ala Glu
        690                 695                 700
Thr Ser Val Asp Arg Asp Gly Asn Gly Phe Thr Gly Lys Gly Glu Ile
705                 710                 715                 720
Glu Ala Lys Pro Phe Tyr Gly Leu Ser Ala Gln Leu Trp Ser Glu Thr
                725                 730                 735
Val Arg Asn Asp Glu Gln Tyr Glu Tyr Met Val Phe Pro Arg Val Leu
                740                 745                 750
Ala Ala Ala Gln Arg Ala Trp His Arg Ala Asp Trp Glu Asn Asp Tyr
                755                 760                 765
Lys Val Gly Val Glu Tyr Ser Gln Asn Ser Asn Leu Val Asp Lys Ala
```

| | | | | | | | | | | | | |
|---|---|---|---|---|---|---|---|---|---|---|---|---|
| | 770 | | | | 775 | | | | | 780 | | |
| Ser | Leu | Asn | Gln | Asp | Tyr | Asn | Arg | Phe | Ala | Asn | Val | Leu | Gly | Gln | Arg |
| 785 | | | | | 790 | | | | | 795 | | | | | 800 |
| Glu | Leu | Ala | Lys | Leu | Glu | Lys | Ser | Gly | Ile | Asp | Tyr | Arg | Leu | Pro | Val |
| | | | | 805 | | | | | 810 | | | | | 815 | |
| Pro | Gly | Ala | Lys | Val | Glu | Asp | Gly | Lys | Leu | Ala | Met | Asn | Val | Gln | Phe |
| | | | | 820 | | | | | 825 | | | | | 830 | |
| Pro | Gly | Val | Thr | Leu | Gln | Tyr | Ser | Leu | Asp | Gly | Glu | Asn | Trp | Leu | Thr |
| | | | 835 | | | | | 840 | | | | | 845 | | |
| Tyr | Ala | Asp | Asn | Ala | Arg | Pro | Asn | Val | Thr | Gly | Glu | Val | Phe | Ile | Arg |
| | | 850 | | | | | 855 | | | | | 860 | | | |
| Ser | Val | Ser | Ala | Thr | Gly | Glu | Lys | Val | Ser | Arg | Ile | Thr | Ser | Val | Lys |
| 865 | | | | | 870 | | | | | 875 | | | | | 880 |

US 6,838,239 B1

CHITOBIASE AS A REPORTER ENZYME

RELATED APPLICATIONS

This application claims priority to U.S. Provisional Patent Application Ser. No. 60/159,221, filed Oct. 13, 1999, the disclosure of which is incorporated herein by reference in its entirety.

GOVERNMENT INTEREST IN THE INVENTION

Work performed in developing the present invention was supported, in part, by National Science Foundation grant MCB-9507209, NIH MBRS grant GM45765, and NIH NIGMS MARC F31 GM14967-0451. Accordingly, the United States Government may have certain rights in the invention.

BACKGROUND OF THE INVENTION

Field of the Invention

Reporter enzymes are enzymes whose activities are easily assayed when present inside cells. In order to study the regulation of a gene whose expression is regulated by various environmental and/or cellular factors or influences, a gene encoding a reporter enzyme may be fused to the coding region or to the regulatory region of the regulated gene.

One of the most popular cytoplasmic reporter enzymes for use in bacteria is β-galactosidase. It is widely used in the art; however, because bacteria such as *Escherichia coli* contain an endogenous β-galactosidase encoding gene and β-galactosidase may be present in the cytoplasm of such bacteria, deletions of the LacZ gene, the source of the enzyme, must be introduced into the host cell line prior to its use. One goal of the present invention is to provide an alternative intracellular enzyme for use as a reporter.

This invention relates to genetic constructs and methods of using a cytoplasmic form of the chitobiase enzyme as a reporter. The invention also comprises expression vectors which express the cytoplasmic form of chitobiase. As used herein, all instances of the terminology "chitobiase" refer to a form of chitobiase which is present in the cytoplasm of the cell. Cytoplasmic forms of chitobiase may be generated via genetic engineering or microbial selection techniques.

SUMMARY OF THE INVENTION

One embodiment of the present invention is a method for characterizing a promoter comprising providing a construct comprising the promoter operably linked to a nucleic acid encoding a cytoplasmic form of chitobiase, introducing the construct into host cells, and identifying sequences in the promoter which regulate transcription levels. In one aspect of this embodiment, the cytoplasmic form of chitobiase lacks a signal sequence. In another aspect of this embodiment, the nucleic acid encoding a cytoplasmic form of chitobiase encodes a fusion protein which comprises a cytoplasmic form of chitobiase fused to a heterologous polypeptide. In still another aspect of this embodiment, the nucleic acid encoding a cytoplasmic form encodes a cytoplasmic form of chitobiase obtained from an organism selected from the group consisting of Alteromonas sp. 0–7, *Arabidopsis thaliana*, *Bacillus subtilis*, *Bombyx mori*, *Bos taurus*, *Caenorhabditis elegans*, *Candida albicans*, *Dictyostelium discoideum*, *Entamoeba histolytica*, *Felis catus*, *Homo sapiens*, Korat cats, *Lactobacillus casei*, *Leishmania donovani*, *Mus musculus*, *Pisum sativum*, *Porphyromonas gingivalis*, Pseudoalteromonas sp. S9, *Raitus norvegicus*, *Serratia marcescens*, *Streptomyces plicatus*, *Streptomyces thermoviolaceus*, *Sus scrofa*, *Trichoderma harzianum*, *Vibrio furnissii*, *Vibrio harveyi*, *Vibrio parahaemolyticus*, and *Vibrio vulnificus*. In a further aspect of this embodiment, the method of identifying sequences which are involved in directing transcription comprises mutagenizing the promoter. In another aspect of this embodiment, the method of identifying sequences which are involved in transcription comprises constructing deletions in the promoter.

Another embodiment of the present invention is a method for identifying a regulatory element capable of directing or regulating transcription within a test nucleic acid sequence comprising providing a construct comprising the test nucleic acid sequence operably linked to a nucleic acid encoding a cytoplasmic form of chitobiase, introducing the construct into host cells, and determining the level of chitobiase activity. In one aspect of this embodiment, the cytoplasmic form of chitobiase lacks a signal sequence. In another aspect of this embodiment, the nucleic acid encoding a cytoplasmic form of chitobiase encodes a fusion protein, the fusion protein comprising a cytoplasmic form of chitobiase fused to a heterologous polypeptide. In still another aspect of this embodiment, the nucleic acid encoding a cytoplasmic form encodes a cytoplasmic form of chitobiase obtained from an organism selected from the group consisting of Alteromonas sp. 0–7, *Arabidopsis thaliana*, *Bacillus subtilis*, *Bombyx mori*, *Bos taurus*, *Caenorhabditis elegans*, *Candida albicans*, *Dictyostelium discoideum*, *Entamoeba histolytica*, *Felis catus*, *Homo sapiens*, Korat cats, *Lactobacillus casei*, *Leishmania donovani*, *Mus musculus*, *Pisum sativum*, *Porphyromonas gingivalis*, Pseudoalteromonas sp. S9, *Rattus norvegicus*, *Serratia marcescens*, *Streptomyces plicatus*, *Streptomyces thermoviolaceus*, *Sus scrofa*, *Trichoderma harzianum*, *Vibrio furnissii*, *Vibrio harveyi*, *Vibrio parahaemolyticus*, and *Vibrio vulnificus*. In one aspect of this embodiment, the reporter gene construct is introduced transiently. In another aspect of this embodiment, the reporter gene construct is introduced stably. The host cells may be selected from the group consisting of prokaryotic cells and eukaryotic cells. In another aspect of this embodiment, the method further comprises permeabilizing or lysing the host cells. The permeabilizing or lysing step may comprise treating the host cells with toluene. The step of determining the level of chitobiase activity may be selected from the group consisting of measuring the amount of a chemiluminescent product produced from a substrate, measuring the amount of a fluorescent product produced from a substrate, measuring the amount of light absorbed by a product produced from a substrate and measuring a decrease in the amount of a detectable substrate. In another embodiment, the step of determining the level of chitiobiase activity may comprise determining the level of p-nitrophenol released from a substrate. In another aspect of this embodiment, the test nucleic acid sequence comprises a portion of genomic DNA. In a further aspect of this embodiment, the step of determining the level of chitobiase activity comprises determining the level of chitobiase activity after exposing the host cells to a desired set of environmental conditions. In still another aspect of this embodiment, the step of determining the level of chitobiase activity comprises determining the level of chitobiase activity after contacting the host cells with a compound to be tested for its influence on the level of transription from siad regulartory element.

Another embodiment of the present invention is a method of detecting successful transformation, comprising the steps of introducing a nucleic acid encoding a cytoplasmic form of chitobiase into host cells, and detecting chitobiase expression in the host cells.

Another embodiment of the present invnetion is a fusion protein-reporter gene construct comprising a promoter operably linked to a nucleic acid encoding a cytoplasmic form of chitobiase fused in frame with a nucleic acid encoding a heterologous polypeptide, wherein the heterologous polypeptide is not p-galactosidase or a portion thereof, and wherein the heterologous polypeptide does not contain a signal peptide. In one aspect of this embodiment, the nucleic acid encodes a cytoplasmic form of chitobiase obtained from an organism selected from the group consisting of Alteromonas sp. 0–7, *Arabidopsis thaliana, Bacillus subtilis, Bombyx mori, Bos taurus, Caenorhabditis elegans, Candida albicans, Dictyostelium discoideum, Entamoeba histolytica, Felis catus, Homo sapiens, Korat cats, Lactobacillus casei, Leishmania donovani, Mus musculus, Pisum sativum, Porphyromonas gingivalis,* Pseudoalteromonas sp. S9, *Rattus norvegicus, Serratia marcescens, Streptomyces plicatus, Streptomyces thermoviolaceus, Sus scrofa, Trichoderma harzianum, Vibrio furnissii, Vibrio harveyi, Vibrio parahaemolyticus,* and *Vibrio vulnificus.* In another aspect of this embodiment, the nucleic acid further comprises a λ site-specific recombination sequence.

Another embodiment of the present invention is a reporter gene construct comprising plasmid pJMF3.

Another embodiment of the present invention is a reporter gene construct comprising plasmid pJMF4.

Another embodiment of the present invention is a reporter gene construct comprising plasmid pDYK9.

Another embodiment of the present invention is a reporter gene construct comprising plasmid pDYK11.

Another embodiment of the present invention is a host cell comprising a fusion protein-reporter gene construct comprising a promoter operably linked to a nucleic acid encoding a cytoplasmic form of chitobiase fused in frame with a nucleic acid encoding a heterologous polypeptide, wherein the heterologous polypeptide is not β-galactosidase or a portion thereof, and wherein the heterologous polypeptide does not contain a signal peptide. In one aspect of this embodiment, the nucleic acid is integrated into a chromosome of the cell. In another aspect of this embodiment, the nucleic acid is transiently expressed in the host cell.

Another embodiment of the present invention is a nucleic acid encoding a cytoplasmic form of chitobiase in which the signal sequence of native chitobiase has been inactivated or deleted. In one aspect of this embodiment, the signal sequence has been mutated to inactivate it.

An isolated or purified polypeptide comprising a cytoplasmic form of chitobiase fused in frame with a heterologous polypeptide, wherein the heterologous polypeptide is not β-galactosidase or a portion thereof and wherein the heterologous polypeptide does not contain a signal peptide.

Another embodiment of the present invention is an isolated or purified polypeptide comprising a cytoplasmic form of chitobiase in which the signal peptide of native chitobiase has been inactivated or deleted. In one aspect of this embodiment, the signal sequence has been mutated to inactivate it.

Another embodiment of the present invention is a method for monitoring the activity of a promoter comprising providing a construct comprising the promoter operably linked to a nucleic acid encoding a cytoplasmic form of chitobiase, introducing the construct into host cells, and determining the level of chitobiase activity. In one aspect of this embodiment, the cytoplasmic form of chitobiase lacks a signal sequence. In another aspect of this embodiment, the nucleic acid encoding a cytoplasmic form of chitobiase encodes a fusion protein, the fusion protein comprising a cytoplasmic form of chitobiase fused to a heterologous polypeptide. In one aspect of this embodiment, the nucleic acid encoding a cytoplasmic form encodes a cytoplasmic form of chitobiase obtained from an organism selected from the group consisting of Alteromonas sp. 0–7, *Arabidopsis thaliana, Bacillus subtilis, Bombyx mori, Bos taurus, Caenorhabditis elegans, Candida albicans, Dictyostelium discoideum, Entamoeba histolytica, Felis catus, Homo sapiens, Korat cats, Lactobacillus casei, Leishmania donovani, Mus musculus, Pisum sativum, Porphyromonas gingivalis,* Pseudoalteromonas sp. S9, *Rattus norvegicus, Serratia marcescens, Streptomyces plicatus, Streptomyces thermoviolaceus, Sus scrofa, Trichoderma harzianum, Vibrio furnissii, Vibrio harveyi, Vibrio parahaemolyticus,* and *Vibrio vulnificus.* In another aspect of this embodiment, the reporter gene construct is introduced transiently. In still another aspect of this embodiment, the reporter gene construct is introduced stably. In a further aspect of this embodiment, the host cells are selected from the group consisting of prokaryotic cells and eukaryotic cells. In yet another aspect of this embodiment, the method further comprises permeabilizing or lysing the host cells. For example, the permeabilizing or lysing step may comprise treating the host cells with toluene. In yet another aspect of this embodiment, the step of determining the level of chitobiase activity may be selected from the group consisting of measuring the amount of a chemiluminescent product produced from a substrate, measuring the amount of a fluorescent product produced from a substrate, measuring the amount of light absorbed by a product produced from a substrate and measuring a decrease in the amount of a detectable substrate. In still another aspect of this embodiment, the step of determining the level of chitiobiase activity comprises determining the level of p-nitrophenol released from a substrate. In still another aspect of this embodiment, the step of determining the level of chitobiase activity comprises determining the level of chitobiase activity after exposing the host cells to a desired set of environmental conditions. In a further aspect of this embodiment, the step of determining the level of chitobiase activity comprises determining the level of chitobiase activity after contacting the host cells with a compound to be tested for its influence on the level of transription from siad regulartory element. For example, the compound may comprise a compound to be tested for activity as a drug.

DETAILED DESCRIPTION OF THE PREFERRED EMBODIMENT

Figure 1:
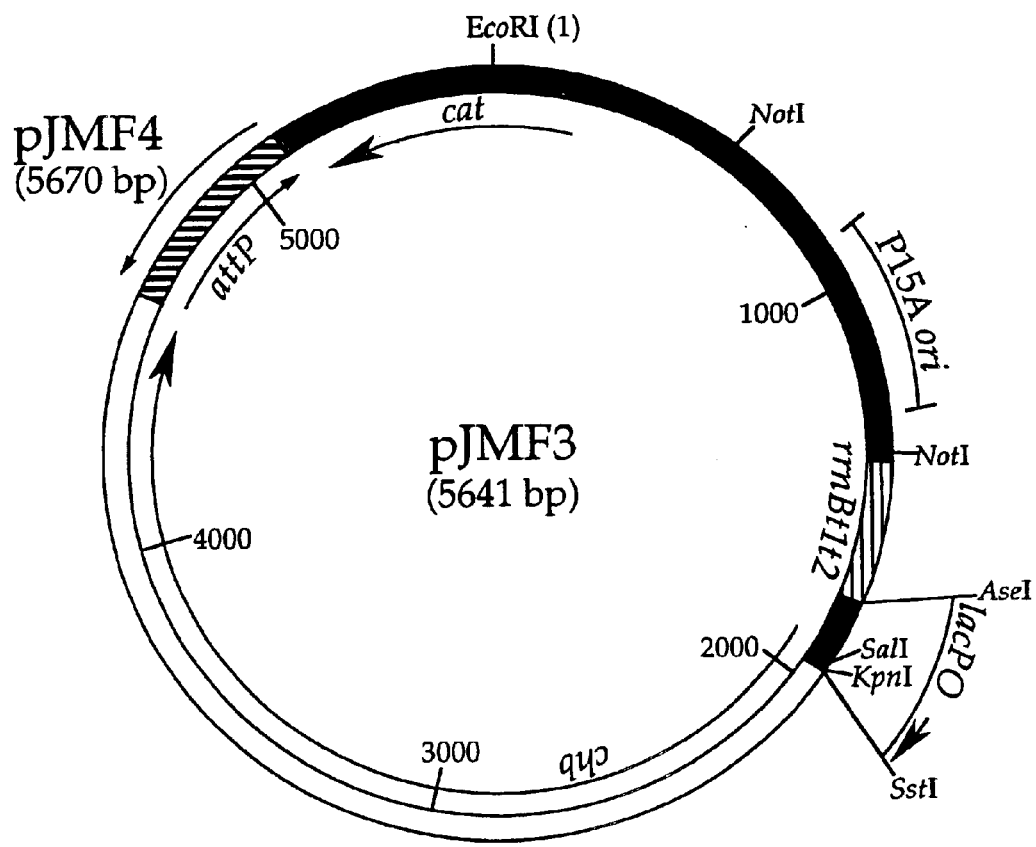
FIG. 1 illustrates plasmids pJMF3 and pJMF4 containing attP in 2 different orientations and the lac promoter with the first 21 amino acids of lacZα (from pUC19) fused in-frame to the chb gene. The sequence of the fusion region is shown in FIG. 2. Restriction sites shown are found once in the plasmid sequences except for NotI, which has 2 sites flanking the P15A origin.

Reporter genes and reporter gene constructs play a number of important roles in a variety of molecular biology techniques. For example, reporter genes may be used to determine whether a sequence contains a promoter or other cis-acting element which directs transcription, such as an enhancer. In addition, reporter genes may be used to identify regulatory sites in promoters or other cis-acting elements and to determine the effects of mutating these regulatory sites on the level of gene expression directed by the promoters or other cis-acting elements. Reporter genes may also be used to detect successful transformation. In addition, reporter genes may be used to monitor gene expression under various conditions and to identify drugs.

The structure of a reporter gene construct containing the cytoplasmic form of chitobiase will vary according to its purposes. When the reporter gene construct is a vector, one must decide between a vector that incorporates the reporter gene into the host's genome or one that replicates extrachromosomally, such as a plasmid. When the reporter construct is not designed to integrate into the host genome, the vector can contain an origin of replication with activity in the host cell of interest. This feature provides the reporter gene vector the ability to replicate within the host cell in which it has been introduced. In addition to the origin of replication, reporter constructs often contain a promoter, a multiple cloning site, a selectable marker, and of course a reporter gene. Reporter constructs for use in eukaryotic cells may also contain a polyA site adjacent to the reporter gene.

Given the utility of reporter gene constructs, it is not surprising that a number of cytoplasmic reporter gene constructs and different reporter genes are available for use by those of skill in the art. For example, the cytoplasmic reporter enzymes chloramphenicol acetyltransferase (CAT), firefly luciferase, β-glucuronidase (GUS), green fluorescent protein (GFP), and β-galactosidase have been used extensively. However, such reporters all have individual shortcomings that may limit or preclude their usage under some conditions. For example, high levels of GFP are toxic to the cell. In addition, reporter enzymes are not expressed equally in all cell types nor are they equally stable when expressed in all cell types. Furthermore, there is a recognized need for multiple reporter enzymes that can be assayed independently of one another in order to simultaneously study the regulation of multiple genes within a single cell type. Therefore, there exists a continuing need to identify reporter enzymes with useful properties.

The cytoplasmic enzyme β-galactosidase is widely used as a reporter gene in various microbiological and molecular biological studies. This enzyme is used in both in vitro and in vivo assays. The wide acceptance of this reporter system results, in part, because it is non-isotopic and extremely flexible. It is used in a number of assay formats and has an extremely broad liner range. Nevertheless, because β-galactosidase is present in the cytoplasm of various host cells such as *Escherichia coli*, deletion of the lacZ gene, the source of the enzyme, is often required prior to its use in a host cell system. One goal of the present invention was to provide an alternative intracellular enzyme for use as a reporter.

An extensive discussion of various molecular biology techniques is available in Ausubel, et al., (eds) "Short Protocols in Molecular Biology," Wiley and Sons, Inc., New York (1997), the disclosures of which are incorporated herein by reference in their entireties. Examples of such techniques include isolating and preparing DNA for manipulation, gel electrophoresis, polymerase chain reaction (PCR), determining nucleic acid sequences, screening nucleic acid libraries, mutagenesis of DNA, and introducing DNA into host cells.

The structure of a reporter gene construct will vary according to its purposes. The reporter gene constructs are constructed according to standard techniques of molecular biology well known in the art.

When the reporter gene construct is a vector, one must decide between a vector that incorporates the reporter gene into the host's genome or one that replicates extrachromosomally, such as a plasmid. When integration of the reporter gene is a desired result, a reporter gene construct will contain sequences that will facilitate incorporation.

One example of integration sequences that can be included in a reporter gene construct is the λ attP site. This site permits a single copy of the reporter gene to be incorporated into a host bacterial genome. Integration-promoting sequences with utility in mammalian cells include the long terminal repeats found in retroviral genomes. These sequences promote viral genome integration in a host genome and have been used extensively by those of skill in the art to promote the integration of exogenous sequences in mammalian host cells.

When the reporter construct is not designed to integrate into the host genome, it is common that the vector contain an origin of replication with activity in the host cell of interest. This feature provides the reporter gene vector the ability to replicate within the host cell in which it has been introduced.

In addition to the origin of replication, reporter constructs will often contain additional features that promote the expression of the nucleic acid sequence or sequences contained in the construct. These additional sequences can include a polyA site, a multiple cloning site, a drug resistance marker, and of course a reporter gene.

The present invention relates to the use of chitobiase as a reporter gene. The chitobiase may be used as a reporter in bacteria, plants, mammalian cells and other host cell lines. One possible alternative to using β-galactosidase as a reporter gene was to develop cytoplasmic N,N'-diacetylchitobiase (N-acetyl-β-D-glucosaminidase, EC 3.2.1.30) for use as a reporter enzyme. One advantage of the enzyme N-acetyl-β-D-glucosaminidase or "chitobiase" over β-galactosidase is that genes encoding chitobiase are missing from many bacteria, including E. coli, some fungi, and some eukaryotic cells. Thus, it is not necessary to engineer many host cells to lack reporter activity as is the case with β-galactosidase. The present invention also relates to various protein expression vectors that can be used to express the reporter gene. In addition, the present invention may be used in conjunction with other reporter enzymes in systems in which the regulation or activities of multiple genes is to be studied simultaneously.

Chitobiase is one of two enzymes that hydrolyze chitin, an abundant insoluble polysaccharide, to its monomeric unit, N-acetylglucosamine (GlcNac). Chitobiase is known to be present in a number of organisms. For example, the chitobiase enzyme is known to be present in various genera including Arabidopsis, Bacillus, Bombyx, Bos, Caenorhabditis, Candida, Dictyostelium, Entamoeba, Felis, Homo, Korat, Lactobacillus, Leishmania, Mus, Pisum, Porphyromonas, Pseudoalteromonas, Rattus, Serratia, Streptomyces, Sus, Trichoderma, and Vibrio. Specific examples of organisms known to contain chitobiase include Alteromonas sp. 0–7, Arabidopsis thaliana, Bacillus subtilis, Bombyx mori, Bos taurus, Caenorhabditis elegans, Candida albicans, Dictyostelium discoideum, Entamoeba histolytica, Felis catus, Homo sapiens, Korat cats, Lactobacillus casei, Leishmania donovani, Mus musculus, Pisum sativum, Porphyromonas gingivalis, Pseudoalteromonas sp. S9, Rattus norvegicus, Serratia marcescens, Streptomyces plicatus, Streptomyces thermoviolaceus, Sus scrofa, Trichoderma harzianum, Vibrio furnissii, Vibrio harveyi, Vibrio parahaemolyticus, and Vibrio vulnificus.

One source of the enzyme is the marine bacterium, Vibrio harveyi. Escherichia coli cells harboring a plasmid carrying the chb gene from Vibrio harveyi were reported to produce the enzyme, which was found to be associated with the outer membrane of the bacterial cells. These are described in Jannatipour, M. et al., "Translocation of Vibrio haneyi N,N'-diacetylchitobiase to the outer membrane of Escherichia coli.," J. Bacteriol. 169:3785–3791 (1987) and Soto-Gil & Zyskind, N,N'-Diacetylchitobiase of Vibrio harveyi primary structure, processing, and evolutionary relationships. J. Biol Chem. 264:14778–14782 (1989), both of which are hereby incorporated by reference.

The present invention contemplates expressed cytoplasmic forms of chitobiase in various forms. In one embodiment, the signal sequence is deleted from the amino terminal portion of the protein. Presumably the removal of this sequence results in the expression of a cytoplasmic form of the enzyme that is not secreted from the host cell or incorporated into the membrane of the host cell producing the enzyme.

The present invention also contemplates the generation of fusion proteins comprising a fusion polypeptide joined in frame to chitobiase. Preferably, the fusion polypeptide comprises a polypeptide other than chitobiase, such as a heterologous protein. The heterologous polypeptide may comprise a polypeptide having a biological activity (such as an enzymatic or other activity besides activity as an immunogen) or the heterologous polypeptide may not have a biological activity. The heterologous polypeptide does not include a signal sequence which directs its secretion. Preferably the heterologous polypeptide is not P-galactosidase or a portion thereof. Thus, the fusion reporter gene construct contains a sequence encoding the fusion polypeptide genetically fused in frame with a sequence encoding chitobiase. In one embodiment, this fusion may remove the amino-terminal signal peptide sequence of chitobiase and replace it with a heterologous protein.

In another embodiment, the fusion protein construct comprises a chitobiase gene sequence that has been truncated to remove at least the signal peptide sequence of the gene. Alternatively, mutations may be introduced into the signal peptide sequence so that it is no longer functional. Such mutations may be introduced using a variety of techniques familiar to those skilled in the art, including site directed mutagenesis, cassette mutagenesis, and chemical mutagenesis.

Once the reporter gene construct is made it is introduced into a host cell line for testing. Host cells of prokaryotic and eukaryotic origin can be used with the reporter gene constructs of the present invention. A variety of methods are available to introduce reporter gene constructs into host prokaryotic cells. For example, bacteria can be transformed using calcium chloride, electroporation, or viral vectors such as the filamentous phages. These and other prokaryotic transformation protocols are well known in the art.

Alternatively, the sequence encoding chitobiase may be introduced in eukaryotic cells, including yeast, mammalian, plant, and insect cells. For example, the sequence encoding chitobiase may be inserted into a yeast artificial chromosome, a yeast plasmid, a bovine papilloma virus vector or other extrachromosomal vector, a retroviral vector, a Ti-plasmid, or a baculovirus vector. A variety of such vectors are known to those skilled in the art. The vectors may be introduced into any of the yeast, mammalian, plant, and insect cells familiar to those skilled in the art.

The introduction of the reporter gene construct into mammalian cells can likewise utilize a number of transfection protocols well known to those of skill in the art. As discussed above, transfections can be transient or stable. Examples of suitable transfer protocols include calcium phosphate transfection, DEAE-Dextran, electroporation, liposome-mediated transfection, and viral transfection. These and other eukaryotic transformation protocols are well known in the art.

Following introduction of the reporter gene construct into the host cell of interest, the enzymatic activity of the reporter gene is measured. Preferably, the chitobiase assays are performed after permeabilizing or lysing the host cells. There are a variety of cell permeabilization and cell lysis procedures available to those of ordinary skill in the art, including methods such as sonication or lysozyme treatment. One embodiment of the present invention uses toluene treatment to permeabilize cells. The details of this method are discussed in D. Y. Kalabat et al., BioTechniques 25:1030–1035 (1998) and Miller, J. H. A Short Course in Bacterial Genetics, CSH Laboratory Press, Cold Spring Harbor, N.Y. 1992, the disclosures of which are incorporated herein by reference in their entireties.

Cellular chitobiase activity can be measured quantitatively by following the hydrolysis of chitobiase substrates. Examples of substrates with utility in chitobiase activity assays include N,N'-diacetylchitobiose (chitobiose), p-nitrophenyl-N-acetyl-β-D-glucosaminide (PNAG)(Sigma Chemical, St. Louis, Mo.), and 5-bromo-4chloro-3-indolyl-N-acetyl-β-D-glucosaminide (X-Gluc)(Sigma Chemical, St. Louis, Mo.). Other substrates are also contemplated for use in the assays of the present invention.

Products produced by the hydrolysis of the chitobiase substrates are monitored using various means familiar to those skilled in the art. For example, various optical means are known to those skilled in the art. One such optical means may comprise detection of chemiluminescent or fluorescent products released from a substrate. Alternatively, the level of chitobiase activity may be determined by measuring the amount of light absorbed by a product produced from a substrate or measuring a decrease in the amount of a detectable substrate. In one embodiment, P-nitrophenol is released from the substrate and measured at 400 nm. Other monitoring methods well known in the art can be used to quantitate signals produced in the chitobiase assay. These may inlcude use of radioactive substrates or substrates having radiofrequency tags. In another embodiment, blue/white colony indicator plates are used to monitor enzyme activity.

Another embodiment of the present invention is a kit. One aspect of this embodiment includes a reporter gene construct comprising a vector containing a chitobiase reporter gene. The reporter gene construct also contains a multiple cloning site containing a variety of restriction endonuclease cutting sites that facilitate the introduction of exogenous DNA into the construct.

The kit embodiment of the present invention also includes those components necessary to assay for chitobiase activity produced by the reporter gene construct. For example, in one embodiment, the kit will include a supply of a suitable chitobiase substrate whose metabolism into product by the reporter enzyme can be assayed.

EXAMPLES

The following Examples are disclosed to assist in the understanding of the present invention. The Examples below should not be construed to limit the scope of the invention and such variations of the invention now known or later developed, which would be within the purview of one of ordinary skill in the art and are considered to fall within the scope of the invention hereinafter claimed.

Example 1

Construction of Vectors

Vectors were constructed using polymerase chain reaction (PCR) products that were cloned first at the SmaI or EcoRV restriction sites of plasmid pBluescript II (pKSII+) (Stratagene; San Diego, Calif.). The nucleotide sequence of all PCR products was determined using standard techniques well known in the art. Unmethylated plasmid DNA was isolated from an *E. coli* dam strain when cutting with the BclI enzyme was required.

The pDYK9 (SEQ ID NO: 11) plasmid was constructed by ligating a SphI-KpnI PCR product containing the dnaA promoter region into plasmid pRSG196 that contains the *V. harveyi* chitobiase gene (see Jannatipour, M., et al.). Briefly, the *V harveyi* chitobiase gene was prepared by cloning a Sau3A partial digest of *V harveyi* DNA into the single BamHI site with the tee gene of pMK2004 [See Soto-Gill & Zyskind, "Cloning of *Vibrio harveyi* chitinase and chitobiase genes in *Escherichia coli*," pp. 209–223, In J. P. Zikakis (ed.), Chitin, chitosan, and related enzymes," Academic Press, Inc., New York (1984)]. The clones containing the gene of interest were detected by the presence of the yellow p-nitrophenylate product after individual colonies of the clone bank were sprayed with 10 mM PNAG dissolved in 100 mM sodium phosphate, pH 7.0. Restriction maps of the positive clones were made according to standard techniques well known in the art.

The chb gene was subcloned in a 3.5-kb EcoRI fragment from pRSG14 [See Jannatipour, M. et al., "Translocation of *Vibrio harveyi* N,N'-diacetylchitobiase to the outer membrane of *Escherichia coli*.," J. Bacteriol. 169:3785–3791 (1987)] into the EcoRi site of pUC19 [Yanisch-Perron, c.J. et al., Gene 33:103–119 (1985)]. Plasmid pRSG196 was constructed by deleting a 0.5-kb SstI fragment from one of these clones [See Jannatipour, M. et al., "Translocation of *Vibrio harveyi* N,N'-diacetylchitobiase to the outer membrane of *Escherichia coli*.," J. Bacteriol. 169:3785–3791 (1987)].

The pRSG196 plasmid was also cut with SphI and KpnI to accommodate the insertion of the dnaA fragment. Plasmid pAC17 [described in Chiaramello & Zyskind, "Coupling of DNA replication to growth rate in *Escherichia coli*: a possible role for guanosine tetraphosphate," J. Bacteriol, 172:2013–2019 (1992) hereby incorporated by reference] served as template with primers 5'-GCA CAT GCA TGC TGG TCA TTA AAT TTT CC-3' (SEQ ID NO 1) and 5'-CGG GGT ACC AAC TCA TCC TGC AAT CG-3' (SEQ ID NO 2) producing a PCR product 374 bp long that contains 353 bp from the dnaA promoter region [bases 583 to 935, numbering according to Hansen, F. G., et al., "The nucleotide sequence of the dnaA gene promoter and of the adjacent rpmH gene, coding for the ribosomal protein L34, of *Escherichia coli*," EMBO J. 1:1043–1048 (1982)]. The forward primer (SphI primer II) contained an SphI site and the reverse primer (KpnI primer) contained a KpnI site for cloning. This created an in-frame fusion between the amino-terminal 17 amino acids of DnaA and the carboxy-terminal end of chitobiase deleted for the amino-terminal 22 amino acids including the signal peptide.

The next step in constructing the pDYK9 vector was taking the 3270 bp DraI-HindIII (partial digest) fragment containing the dnaA-chb fusion and Ligating it to the pACYC184 2555 bp HincII-HindIII fragment carrying chloramphenicol-resistance (Cm$^r$) and the P15A origin. This fragment was described in Chang & Cohen, "Construction and characterization of amplifiable multicopy DNA cloning vehicles derived from the p15A cryptic miniplasmid," J. Bacteriol. 134:1141–1156 (1987).

A NotI site was introduced at the AccI site after digestion with AccI, treatment with Mung bean nuclease, and ligation to phosphorylated NotI linkers (New England Biolabs, Inc.; Beverly, Mass.). A NotI site was introduced at the AseI site after digestion with AseI, treatment with Mung bean nuclease, and ligation to phosphorylated NotI linkers (New England Biolabs, Inc.; Beverly, Mass.). An XbaI-SphI PCR product containing the rrnBt1t2 terminator was ligated into this plasmid cut with the same enzymes creating pDYK7. *E. coli* chromosomal DNA served as template with primers 5'-CTA GTC TAG ATG CCG AAC TCA GAA GTG A-3'

(SEQ ID NO 3) and 5'-GCA CAT GCA TGC GGG GGA TGG CTT GTA GAT-3' (SEQ ID NO 4) to produce a PCR product 357 bp long that contains bases 6534 to 6869 from the rrnB operon [numbering according to Brosius, J., et al., "Gene organization and primary structure of a ribosomal RNA operon from *Escherichia coli*." J. Mol. Biol. 148:107–127 (1981)] and includes the complex transcription termination region of this operon which is described in Orosz, A., et al., "Analysis of the complex transcription termination region of the *Escherichia coli* rrnB gene," Eur. J. Biochem. 201:653–659 (1991). The forward primer contained an XbaI site and the reverse primer contained an SphI site.

A BclI-SmaI PCR product containing the λ attP site was ligated into pDYK7 cut with TthIIII, treated with Mung bean nuclease, then digested with BclI. Plasmid pHN894 [described in Goodman, S. D., et al., "Deformation of DNA during site-specific recombination of bacteriophage lambda: Replacement of IHF protein by HU protein or sequence-directed bends," Proc. Natl. Acad. Sci. USA 89:11910–11914 (1992)] served as template with the forward primer 5'-CAT GAT CAT GCG ACA GGT TTG ATG A-3' (SEQ ID NO 5) and the reverse primer 5'-GGG GGC GCC TAC CTT TCA CGA G-3' (SEQ ID NO 6) producing a PCR product 466 bp long that contains the λ attP site. The 466 bp PCR product containing the λ attP site was first cloned into the SmaI site of the pKSII+ plasmid to produce pDYK8. The forward primer contains a BclI site and the reverse primer contains G's at the 5' end in order to recreate a SmaI site when cloning the PCR fragment into a SmaI site. This PCR product includes bases −211 to +241 from the center of the attP core and the sequence required for optimum λ attP site integration as described in Nagaraja & Weisberg, "Specificity determinants in the attachment sites of bacteriophages HK022 and λ," J. Bacteriol. 172:6540–6550 (1990). The orientation of attP is such that when the fusion is integrated at attB, the transcription direction of dnaA p1 and p2 promoters is the same as replication fork movement mimicking the orientation at the wild type dnaA promoters.

Vector pDYK11 (SEQ ID NO: 12) was constructed by ligating an SphI-KpnI PCR product containing the rpmH-dnaA promoter region into pDYK9 also digested with SphI and KpnI. Plasmid pAC17, described in Chiaramello & Zyskind, (1992), served as template with the primers 5'-CAT GCA TGC ATG AAA CGA TGG ACA CC-3' (SEQ ID NO 7) and 5'-CGG GGT ACC AAC TCA TCC TGC AAT CG-3' (SEQ ID NO 8) to produce a PCR product 616 bp long that contains 598 bp from the rpmH-dnaA regulatory region [bases 338 to 935, numbering according to Hansen, F. G., et al., (1982)]. The forward primer (SphI primer I) contained an SphI site and the reverse primer (KpnI primer) contained a KpnI site for cloning. SEQ ID NO: 18 provides the complete coding sequence of the DNA encoding the dnaA/chitobiase fusion protein. The complete sequence of the dnaA/chitobiase fusion protein is provided in SEQ ID NO: 19.

The vector pJMF3 (SEQ ID NO: 13) was constructed by first ligating an AseI linker (5'-CATTAATGCATG-3' (SEQ ID NO 9) self-hybridized) into the SphI site of pDYK11. The pUC19, [described in Yanisch-Perron C., et al., "Improved M13 phage cloning vectors and host strains: nucleotide sequences of the M13mp18 and pUC19 vectors," Gene 33:103–19 (1985)] AseI-KpnI fragment containing the lacPO-polylinker region was ligated to this plasmid after digestion with AseI and KpnI. The resulting in-frame fusion between the amino-terminal 21 amino acids of the pUC19 lacZ(α) peptide [Yanisch-Perron C., et al., 1985] and the carboxy-terminal end of chitobiase deleted for the amino-terminal 22 amino acids is identical to the protein fusion in pRSG196 [Jannatipour, M., et al., (1995)].

Vector pJMF4 (SEQ ID NO: 14 ) was constructed by ligating the BamHI-EcoRV fragment of pDYK8 containing the λ attP site into pDYK7 which had been digested with TthIIII , treated with Mung bean nuclease, then digested with BclI, to create pTKP9. This reversed the orientation of the attP site relative to the attP site in pDYK9. The pDYK11 BspMII-KpnI fragment containing the rpmH-dnaA promoter region was then ligated into pTKP9 digested with the same enzymes to create pTKP11. This reversed the orientation of the attP site relative to the attP site in pDYK11. An AseI linker (5'-CATTAATGCATG-3' (SEQ ID NO 10) self-hybridized) was ligated into the SphI site of pTKP11 to create pJMF2. The pUC19 [as described in Yanisch-Perron C., et al., (1985)] AseI-KpnI fragment containing the lacPO-polylinker region was ligated to pJMF2 cut with AseI and KpnI to create pJMF4.

Example 2

Site-specific Recombination

To move the chitobiase fusions in pDYK9 and pDYK11 to the attB site in the chromosome, NotI fragments from these plasmids were self-ligated and transformed or electroporated into strain WM2269 (DH5α containing pLDR8) [See Zyskind, J. W. and S. I. Bernstein (1992) "Recombinant DNA Laboratory Manual," Academic Press, San Diego, Calif.]. Plasmid pLDR8, described in Diederich, L. L. J., et al., "New cloning vectors for integration into the A attachment site attB of *Escherichia coli* chromosome," Plasmid 28:14–24 (1992), expresses integrase from the λ $P_R$ promoter and contains the λ $cI_{857}$ repressor gene, a kanamycin resistance gene, and a temperature-sensitive origin of replication. The transformed or electroporated cells were incubated at 42° C. with shaking for 30 min then moved to 37° C. for 1 h followed by selection on Luria broth agar plates containing chloramphenicol (25 μg/ml) at 42° C. Transformants were screened for loss of kanamycin resistance and, therefore, loss of pLDR8.

Example 3

Bacteriophage P1 Transduction

Transduction with P1 bacteriophage by the method of Zyskind & Bernstein, Recombinant DNA Laboratory Manual. Academic Press, San Diego, Calif. (1992) was used to construct strains and to confirm the chromosomal location of the dnaA-chb fusions. Cotransduction of $Cm^r$ (carried by the fusion) and galK (linked to attB) indicated that $Cm^r$ and galK are linked on the chromosomes of strains DYK9W, DYK9F, DYK11W, and DYK11F.

Example 4 p-Nitrophenol Chitobiase Activity Assay

Chitobiase activity is located in the cytoplasm when its signal peptide is replaced by fusion with another peptide. Accordingly, chitobiase assays are performed on permeabilized or lysed cells. A variety of permabilization or cell lysis protocols are available to liberate the enzyme from within a cell population being tested. One such protocol involves toluene-treated cells washed once with M9 salts according to the method of Miller, J. H. A Short Course in Bacterial Genetics, CSH Laboratory Press, Cold Spring Harbor, N.Y.

1992, which is hereby incorporated by reference. The toluenized cells are placed in a chitobiase buffer (10 mM Tris-HCl, pH 8.0, and 0.5 M NaCl) and 666 µM PNAG, the chitobiase enzyme substrate. NaCl is included because chitobiase has approximately 80% of full activity in the absence of salt, with maximal activity occurring between 0.25 and 0.6 M NaCl. Toluenized cells (0.772 ml) are preincubated at 28° C. and the reaction started with the addition of 0.228 ml PNAG (1 mg/ml). After incubation at 28° C., the reaction is stopped by the addition of 1 ml of 1 M Tris base. The release of p-nitrophenol is measured at 400 nm and turbidity at 550 nm. p-Nitrophenol release is measured immediately at 400 nm with a molar absorptivity of $1.8 \times 10^3$ liters $mol^{-1}$ $cm^{-1}$. Units are calculated after subtracting the light scattering factor ($1.5 \times OD_{550}$) from $OD_{400}$ of the sample. The normalizing factor of 1.5 was determined previously by measuring the light scattering ratio of bacteria at $OD_{400}$ and $OD_{550}$. One unit of chitobiase activity is the amount of enzyme that catalyzes the formation of 1 pmol of p-nitrophenol per min at 28° C. For comparison to Miller units of β-galactosidase [described in Miller, J. H., A Short Course in Bacterial Genetics. Cold Spring Harbor Laboratory Press, Cold Spring Harbor, N.Y. (1992)], the units are normalized to 1 ml of culture at $OD_{450}=1$.

Example 5

Determination of Chitobiase Activity in Cells Containing Vectors pJM3 and pJM4

(FIG. 1) contain the lacPO promoter with the first 21 amino acids of lacZα (from pUC19) fused in-frame to the chb gene. These plasmids also contain the λ phage attP recombination site in different orientations, the gene encoding chloramphenicol acetyltransferase (cat), and a ribosomal terminator, rrnBt1t2, inserted upstream of the lac-chb fusion to prevent read-through from other promoters. The chitobiase activity associated with these plasmids (Table 1) is high in the absence of IPTG because of titration of lac repressor expressed from a single copy chromosomal gene. Induction by IPTG is approximately 10-fold (Table 1).

TABLE 1

Chitobiase Activity of lacZ-chb Fusion[a]

| | Chitobiase[b] (U[c]) | |
|---|---|---|
| Plasmid | −IPTG | +IPTG (1 mM) |
| pJMf3 in DH5α | 668 ± 45 | 9320 ± 347 |
| pJMF4 in DH5α | 788 ± 44 | 7188 ± 477 |

[a]Overnight cultures were diluted 1:1000 into 50 mL prewarmed LB and grown to $OD_{450}$ = 0.1. 1 mM IPTG was added to half of the culture, and growth continued to $OD_{450}$ = 0.3.
[b]Triplicate samples were assayed. Mean chitobiase activities are given with standard deviations.
[c]One unit of chitobiase activity is 1 pmol of p-nitrophenol/min at 28° C. Units given for 1 mL of culture at $OD_{450}$ = 1.

Figure 2:
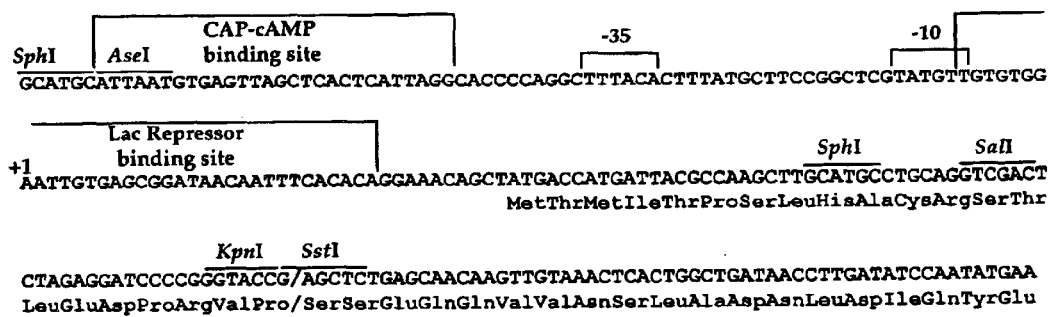
FIG. 2 illustrates the sequence of the lac promoter and the chitobiase fusion found in pJMF3 and pJMF4 (SEQ ID NOS: 15 and 16). Fusion between lacZα (from pUC19) and chb [Soto-Gill, R. W. et al, J. Biol. Chem. 264:14778–14782 (1998)] is indicated by (/); start of transcription is indicated by (+1). Sequence and binding sites in the lac promoter regulatory region are found in Dickson, R. C. et al., Science 187:27–32 (1975), the disclosure of which is incorporated herein by reference in its entirety. Restriction enzyme sites shown in FIG. 2 are found once in the plasmid sequences except for SphI, which has 2 sites; these different restriction sites can be used to replace the lac promoter with another promoter together with part of a coding region to produce an in-frame fusion with chb.
Figure 3:
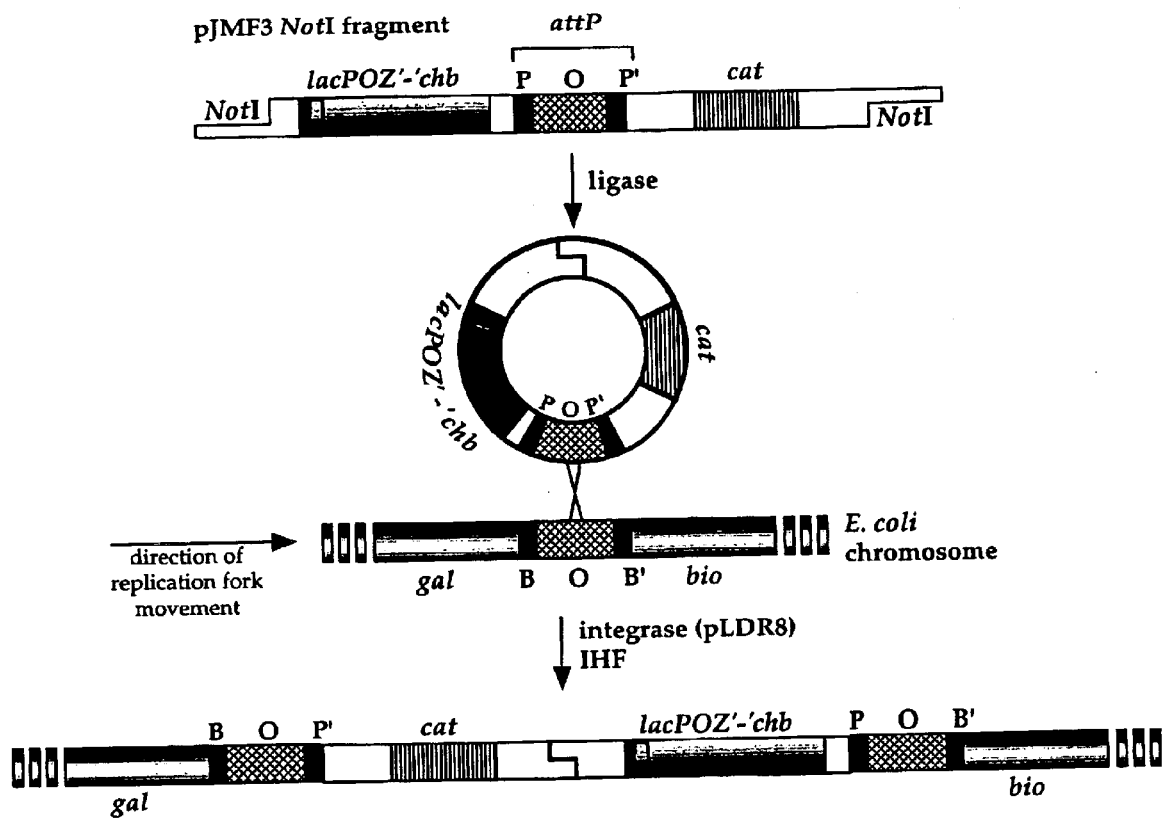
FIG. 3 depicts integration of chb fusions into the chromosome by site-specific recombination between attB and attP. The steps involved are described below and in Diederich, L. L, et al., Plasmid 28:14–24 (1992), the disclosure of which is incorporated herein by reference in its entirety.

The lac promoter can be replaced with another promoter and a fusion protein created with chitobiase by cutting with SphI or AseI and either SalI, KpnI, or SstI (FIG. 2). Fusions created with these vectors can be moved to the chromosome by site specific recombination at the λ attB site to permit single copy analysis of the activity of the promoter. The protocol, as described more fully in Diederich, et al., "New cloning vectors for integration into the λ attachment site attB of *Escherichia coli* chromosome," Plasmid 28:14–24 (1992), involves two components, (i) a circular DNA containing the λ attachment site, attP, the promoter-chb gene fusion, and the cat gene, and (ii) a helper plasmid, pLDR8, which contains the int gene under the control of the temperature-sensitive repressor, cI857 and a temperature-sensitive origin of replication. The plasmid is digested with NotI to remove the P15A origin, and the fragment containing the chitobiase fusion is self-ligated prior to transformation into cells containing pLDR8. Integration occurs by site-specific recombination between attP and attB (17.4 min on the *E. coli* chromosome, FIG. 3).

Example 6

Use of the Chitobiase Reporter Enzyme to Study dnaA Gene regulation

Figure 4:
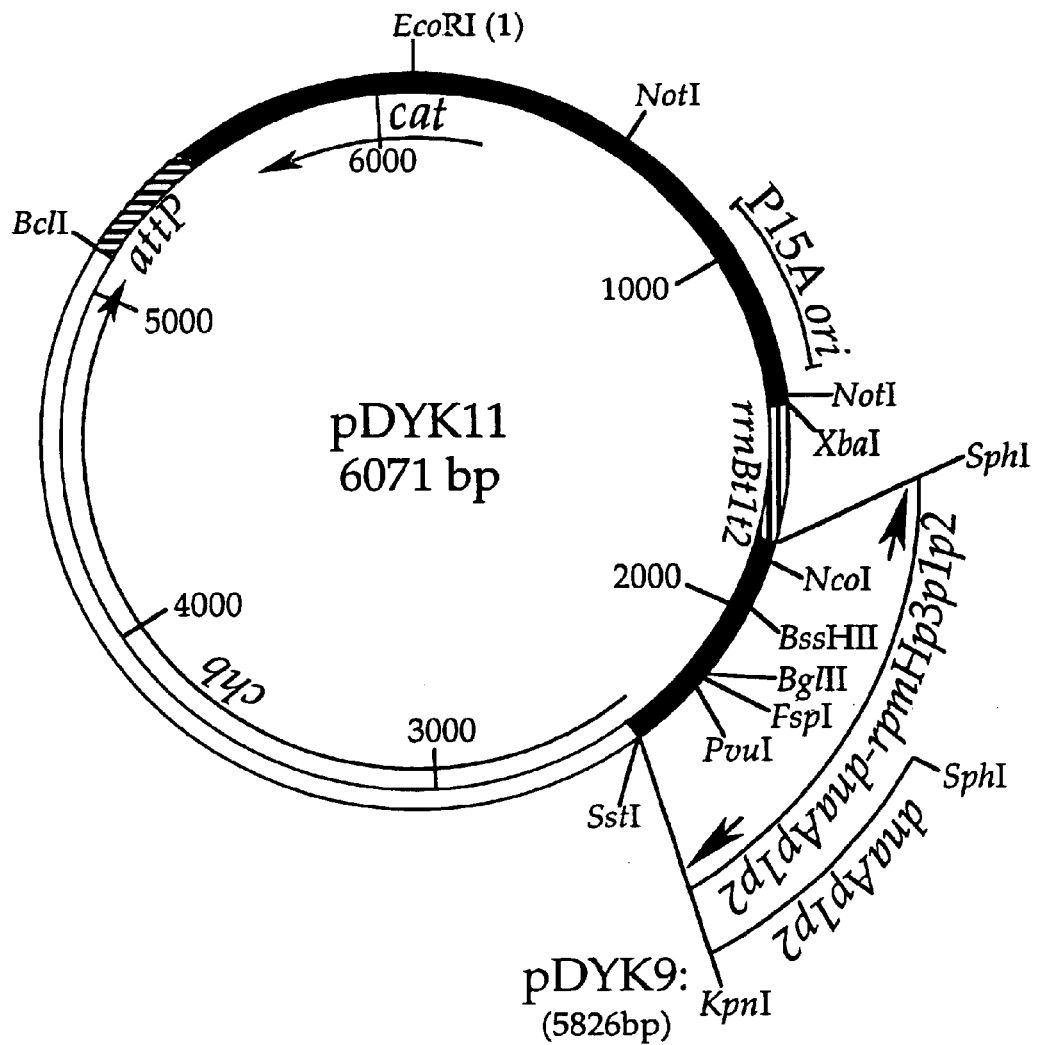
FIG. 4 illustrates plasmids pDYK9 and pDYK11 which contain dnaA-chb fusions. pDYK9 is deleted for the rpmh regulatory region. The orientation of attP in pDYK9 and pDYK11 is the same as that of pJMF3. After integration at attB of the larger NotI fragment, the dnaA promoters are oriented to transcribe in the same direction as replication fork movement.

Two plasmids, pDYK9 and pDYK11, discussed in the Examples above, were constructed to assess the regulation of the dnaA gene using chitobiase as a reporter enzyme. These plasmids differ by the absence of the rpmH regulatory region in pDYK9 (FIG. 4). These fusions were moved from the plasmid to the chromosomal attB site for single copy analysis as described above. After transformation of strain WM2269 with the ligated DNA, integration occurred by site specific recombination between the attP and the attB sites. The orientation of attP in pDYK9 and pDYK11 is such that when the fusion is integrated at attB, the transcription direction of dnaAp1 and dnaAp2 promoters is the same as movement of the replication fork. This orientation is the same as at the dnaA wild type location. The genetic location of the fusions was confirmed in the Cm[r] transformants by demonstrating cotransduction of Cm[r] and galK.

The fusions created in strain WM2269 were moved by P1 transduction to MG1655, creating strain DYK9W with pDYK9 and strain DYK11W with pDYK11. Deletion of the rpmH promoters had very little effect (1.4-fold) on chitobiase activity (Table 2, compare lines 1 and 3)

TABLE 2

Chitobiase and β-Gal Activities of dnaA-chb and dnaA-lacZ Fusions in WT and fis Mutant Backgrounds

| Strains | Chitobiase[a] (U[b]) | βGal[c] (Miller U[d]) |
|---|---|---|
| DYK11W fis+ | 30.0 ± 2.1 | |
| DYK11F fis::985 | 80.0 ± 1.2 | |
| DYK9W fis+ | 44.0 ± 2.1 | |
| DYK9F fis::985 | 96.0 ± 3.5 | |
| RB220 fis+ | | 59.8 ± 7.9 |
| TP220 fis::767 | | 115.2 ± 7.2 |

[a]Triplicate samples were assayed during exponential growth. Mean chitobiase activities are given with standard deviation.
[b]One unit of chitobiase activity is 1 pmol of p-nitrophenol per min at 28° C. Units given for 1 mL of culture at $OD_{450}$ = 1.
[c]Data from Reference 8.
[d]Unit defined in Reference 13.

Figure 5:
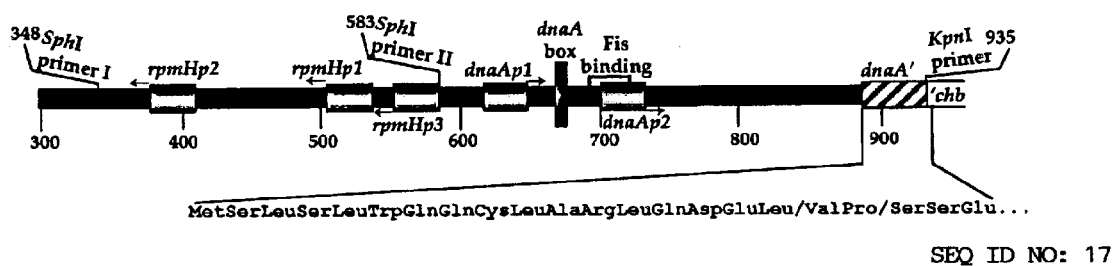
FIG. 5 illustrates the rmpH-dnaA regulatory region and dnaA-chitobiase fusion (SEQ ID NO: 17). The dnaA box and promoters are shaded, and the coding region of the dnaA gene is striped. The fusion contains two amino acids (between the backslashes) from pUC19. The region cloned into pDYK9 is between SphI primer II and KpnI primer, and the region cloned into pDYK11 is between SphI primer I and KpnI primer. The numbers above the primers refer to the nucleotide in the sequence amplified. For sequence numbering and the locations of promoters and protein binding sites, see Froelich, J. M. et al., J. Bacteriol. 178:6006–6012 (1996); Hansen, F. G. et al., EMBO J. 1:1043–1048 (1982) and Messer, W. and C. W. Weigel, Initiation of Chromosome Replication. p. 1579–1601 (1996) In F. C. Neidhart, R. Curtiss III, J. L. Ingraham, E. CC. Lin, K. B. Low, B. Magasanik, W. S. Reznikoff, M. Riley, M. Schaechter and H. E. Umbarger (Eds.), *Escherichia coli* and Salmonella Cellular and Molecular Biology., ASM Press, Washington, D.C., the disclosures of which are incorporated herein by reference in their entireties.

Fis protein binds to a site in the dnaAp2 promoter that covers the −35 sequence (FIG. 5), and appears to be a repressor of DnaA expression. A fusion protein with β-galactosidase activity that is expressed from the rpmH-dnaA regulatory region has increased β-galactosidase activity (1.9-fold) in a fis⁻ mutant when compared to Fis wild type cells [as described in Froelich, J. M., et al., "Fis binding in the dnaA operon promoter region," J. Bacteriol. 178:6006–6012 (1996), data shown in Table 3]. Similarly, the absence of Fis leads to a greater than 2-fold increase in chitobiase activity of the DnaA-chitobiase fusion protein for the DYK9F and DYK11F strains, comparable in extent to that observed with the dnaA-lacZ fusion strain, TP220 (Table 3).

In the reporter gene constructs discussed in the Example, all upstream transcriptional activity was prevented from entering the chb reporter gene. The plasmid vectors, pJMF3 and pJMF4, described in the Examples above, contained the rrnbt1t2 terminator upstream of the promoter fusion, which prevented readthrough from chromosomal promoters near the insertion site. Only chitobiase activity originating from the promoters of interest was expressed.

The attP site in these vectors allowed integration at the chromosomal attB in a specific orientation, depending on the vector used. With these vectors, any chitobiase fusion involving an essential gene can be moved to the chromosome, thus permitting single copy analysis with a chromosomal orientation similar to the wild-type gene.

Example 7

Identification of Promoters in Test Sequences

A nucleic acid prospectively containing a promoter is inserted upstream of a nucleic acid encoding a cytoplasmic form of chitobiase as described above. For example, the nucleic acid prospectively containing a promoter may be inserted into a restriction site in a sequence containing a plurality of restriction sites, such as a polylinker, which is located upstream of the nucleic acid encoding chitobiase. The test sequence may comprise any nucleic acid to be tested for promoter activity. In one embodiment, the test sequence may comprise a genomic DNA sequence. For example, the genomic DNA sequence may be a randomly generated DNA fragment, such as a fragment generated using shotgun cloning techniques, a restriction fragment, or any other sequence.

The vectors containing the test sequence upstream of the nucleic acid encoding chitobiase are introduced into an appropriate host cell. The level of chitobiase activity is assayed and compared to the level obtained from a control vector which lacks an insert in the cloning site. The presence of an elevated expression level in cell containing the vector containing the insert with respect to the level in cells containing the control vector without the insert indicates the presence of a promoter in the insert.

In some embodiments, the activity of the promoter in the test sequence may be assayed after exposure of the host cells to conditions which may influence the level of transcription from the promoter. For example, the environment of the host cells may be altered to determine whether the transcription level is influenced by environmental factors, including factors such as temperature, pH, nutrients, or availability of oxygen. In such analyses, chitobiase levels are assayed under a variety of environmental conditions to determine the effects of the environmental conditions on transcription levels from the promoter. In addition, the activity of the promoters may be examined in the presence or absence of compounds to be tested for regulatory activity. For example, the activity of the promoters may be tested by determining the levels of chitobiase produced in the presence or absence of compounds to be tested for activity as drugs.

Promoter sequences within the test sequences may be further defined by constructing nested deletions in the test sequences using conventional techniques such as Exonuclease III digestion. The resulting deletion fragments can be inserted into the promoter reporter vector to determine whether the deletion has reduced or obliterated promoter activity as determined by measuring chitobiase activity in cells containing the deletion vectors. In this way, the boundaries of the promoters may be defined. If desired, potential individual regulatory sites within the promoter may be identified using techniques such as site directed mutagenesis or linker scanning to obliterate potential transcription factor binding sites within the promoter individually or in combination. The effects of these mutations on transcription levels may be determined by inserting the mutations into the cloning sites in the promoter reporter vectors and measuring the levels of chitobiase produced from the mutated promoters.

The activity of known promoters may also be monitored by operably linking them to a nucleic acid encoding a cytoplasmic form of chitobiase. The activity of the promoters may be analyzed under various environmental conditions as described above. In addition, the activity of the promoters may be analyzed in the presence or absence of compounds to be tested for the ability to affect transcription from the promoters. For example, the compounds may be tested for activity as drugs.

In some embodiments, the chitobiase reporter constructs may be used in systems for identifying compounds that modulate cell surface protein-mediated activity or compounds which modulate the activities of intracellular signaling systems. Techniques for using reporter genes to identify compounds which modulate cell surface protein-mediated activity have been described in U.S. Pat. No. 5,401,629 and U.S. Pat. No. 5,436,128, the disclosures of which are incorporated herein by reference in their entireties. Briefly, in such methods, a construct comprising a promoter operably linked to a nucleic acid encoding a reporter enzyme is introduced into cells which express the cell surface protein and cells which do not express the cell surface protein. Each of the cells are contacted with test compounds and the effects of these compounds on transcription levels is measured by determining the level of activity of the reporter enzyme. The level of expression of the reporter gene in cells expressing the cell surface protein is compared to the level in cells which do not express the cell surface protein to identify compounds that modulate cell surface protein activity.

Similarly, the chitobiase reporter constructs may be used to identify compounds which influence the activity of intracellular signaling pathways, such as cAMP-based or phosphorylation-based pathways. In such methods, a promoter which is activated via such pathways is operably linked to a nucleic acid encoding a cytoplasmic form of chitobiase. The cells are contacted with test compounds. Those compounds which activate the pathway to which the promoter responds will produce an enhanced level of chitobiase activity in the cells as compared to the level of chitobiase activity in control cells which have not been contacted with the test compound.

Example 8

Detecting Successful Transformation or Transfection Using Chitobiase

A vector comprising a sequence encoding a cytoplasmic form of chitobiase operably linked to a sequence capable of directing transcription of the chitobiase gene is introduced into a host cell. The host cells are contacted with a chitobiase substrate and those host cells which contain chitobiase activity are identified as cells which were successfully transformed or transfected. In some embodiments, a portion or replica of a colony may be lysed or permeabilized prior and the lysate or permeabilized cells may be contacted with the chitobiase substrate.

Conclusion

New gene reporter systems that use chitobiase have been described. Chitobiase has advantages over other reporter gene systems in that chitobiase is not found in many cell lines traditionally used in reporter gene systems.

Finally, the forgoing examples are not intended to limit the scope of the present invention, which is set forth in the following claims. In particular, various equivalents and substitutions will be recognized by those of ordinary skill in the art in view of the foregoing disclosure, and these are contemplated to be within the scope of the present invention. All references cited herein are incorporated herein by reference in their entireties.

What is claimed is:

1. A method for identifying a regulatory element capable of directing or regulating transcription within a test nucleic acid sequence comprising:

providing a construct comprising said test nucleic acid sequence operably linked to a nucleic acid encoding a cytoplasmic form of chitobiase;

introducing said construct into host cells; and determining the level of chitobiase activity.

2. The method of claim 1, wherein said cytoplasmic form of chitobiase lacks a signal sequence.

3. The method of claim 2, wherein said nucleic acid encoding a cytoplasmic form of chitobiase encodes a fusion protein, said fusion protein comprising a cytoplasmic form of chitobiase fused to a heterologous polypeptide.

4. The method of claim 1, wherein said nucleic acid encoding a cytoplasmic form encodes a cytoplasmic form of chitobiase obtained from an organism selected from the group consisting of Alteromonas sp. 0–7, *Arabidopsis thaliana, Bacillus subtilis, Bombyx mori, Bos taurus, Caenorhabditis elegans, Candida albicans, Dictyostelium discoideum, Entamoeba histolytica, Felis catus, Homo sapiens*, Korat cats, *Lactobacillus casei, Leishmania donovani, Mus musculus, Pisum sativum, Porphyromonas gingivalis*, Pseudoalteromonas sp. S9, *Rattus norvegicus, Serratia marcescens, Streptomyces plicatus, Streptomyces thermoviolaceus, Sus scrofa, Trichoderma harzianum, Vibrio furnissii, Vibrio harveyi, Vibrio parahaemolyticus*, and *Vibrio vulnificus*.

5. The method of claim 1, wherein said reporter gene construct is introduced transiently.

6. The method of claim 1, wherein said reporter gene construct is introduced stably.

7. The method of claim 1, wherein said host cells are selected from the group consisting of prokaryotic cells and eukaryotic cells.

8. The method of claim 1, further comprising permeabilizing or lysing said host cells.

9. The method of claim 8, wherein said permeabilizing or lysing step comprises treating said host cells with toluene.

10. The method of claim 1, wherein said step of determining the level of chitobiase activity is selected from the group consisting of measuring the amount of a chemiluminescent product produced from a substrate, measuring the amount of a fluorescent product produced from a substrate, measuring the amount of light absorbed by a product produced from a substrate and measuring a decrease in the amount of a detectable substrate.

11. The method of claim 1, wherein said step of determining the level of chitobiase activity comprises determining the level of p-nitrophenol released from a substrate.

12. The method of claim 1, wherein said test nucleic acid sequence comprises a portion of genomic DNA.

13. The method of claim 1, wherein said step of determining the level of chitobiase activity comprises determining the level of chitobiase activity after exposing said host cells to a desired set of environmental conditions.

14. The method of claim 1, wherein said step of determining the level of chitobiase activity comprises determining the level of chitobiase activity after contacting said host cells with a compound to be tested for its influence on the level of transcription from said regulatory element.

* * * * *